US006432657B1

(12) United States Patent
Kikuchi et al.

(10) Patent No.: US 6,432,657 B1
(45) Date of Patent: *Aug. 13, 2002

(54) METHOD FOR DETERMINING COAGULATION PARAMETERS

(75) Inventors: Masayoshi Kikuchi, Choshi; Shin Watanabe; Yoshimichi Yoshimura, both of Tsukuba, all of (JP)

(73) Assignees: Tokuyama Corporation, Yamaguchi; A & T Corporation, Tokyo, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/463,364

(22) PCT Filed: Jul. 22, 1998

(86) PCT No.: PCT/JP98/03263

§ 371 (c)(1),
(2), (4) Date: Jan. 24, 2000

(87) PCT Pub. No.: WO99/05312

PCT Pub. Date: Feb. 4, 1999

(30) Foreign Application Priority Data

Jul. 23, 1997 (JP) .............................................. 9-197006

(51) Int. Cl.[7] .......................... C12Q 1/56; C12Q 1/00; G01N 33/86
(52) U.S. Cl. ................................ 435/13; 435/4; 436/69
(58) Field of Search .......................... 435/13, 4; 436/69

(56) References Cited

U.S. PATENT DOCUMENTS 5,292,664 A  *  3/1994  Fickenscher
5,508,202 A  *  4/1996  Enomoto et al.
5,552,296 A     9/1996  Adema et al. ................. 435/13
5,563,041 A  * 10/1996  Reers

FOREIGN PATENT DOCUMENTS

JP         7-255497          10/1995

OTHER PUBLICATIONS

Derwent abstract (Acc No 1995–195689) of EP 655627A2.
Thomas et al. (1995). Assay methods for detecting the fibrin breakdown product D–dimer—for diagnosing and monitoring thrombolytic and hyper–coagulable states.*
CAPLUS abstract (Acc No 1978:558988). Laudano et al. (1978). Synthetic peptide derivatives that bind to fibrinogen to prevent the polymerization of fibrin monomers.*
D. Rijkers et al., "Prevention of the Influence of Fibrin and $\alpha_2$–Macroglobulin in the Continuous Measurement of the Thrombin Potential: Implications for an Endpoint Determination of the Optical Density", Thrombosis Reserach, vol. 89, (1998) pp. 161–169.
Lab. Delo, vol. 0, No. 7 (1981) Ponizouskii M.R., et al., "Determination of disturbance in polymerization phase of blood coagulation", pp. 416–418, with English abstract.

* cited by examiner

Primary Examiner—Ralph Gitomer
Assistant Examiner—Mahreen Chaudhry
(74) Attorney, Agent, or Firm—Wenderoth, Lind & Ponack, L.L.P.

(57) ABSTRACT

A method for determining coagulation parameters which is safe, convenient, applicable to existing automated analyzers and reliable is disclosed. The said method for the determination utilizes an antibody against the E region of fibrinogen, fibrinogen degradation product D dimer or the like, and is enable to determine the coagulation parameter in fibrin coagulation system accompanied by limited degradation of fibrinogen with thrombin without clotting.

12 Claims, 12 Drawing Sheets

Molar ratio of anti-FgDP-E antibody/fibrinogen

METHOD FOR DETERMINING COAGULATION PARAMETERS

BACKGROUND OF THE INVENTION

1. Field of the Invention

The invention mainly relates to a method to determine coagulation parameters such as prothrombin time, activated partial thromboplastin time and the like in a sample containing fibrinogen, for example a plasma sample, as well as to a kit to conduct the method. As one of the features of the invention is that since the coagulation parameters can be measured without making a sample completely clotted, an automated analyzer can be easily applied to the operation.

2. Description of the Related Art

Currently, most of the methods for measuring (or determining) the coagulation parameters in a sample containing fibrinogen such as a plasma sample, are based on addition of a blood coagulation reagent to the sample in a reaction vessel, incubation thereof, and optical or physical detection of the resulting fibrin clot. Specifically, the coagulation parameters are measured by monitoring the degree of an increase in turbidity or viscosity of a sample accompanied by the production of stable fibrin from the fibrin clotting process illustrated hereinafter.

Accordingly, fibrin clot which occurs when a blood coagulation reagent is added to a fibrin-containing sample is roughly composed of (1) a process in which a coagulation cascade reaction starts to produce thrombin, (2) a process in which the produced thrombin react as a catalyst upon fibrinogen existing in the sample to make fibrinopeptide A freed from the A$\alpha$ chain of fibrinogen and fibrinopeptide B freed from the B$\beta$ chain, and to produce a fibrin monomer on which E region the polymerization site "A" and the polymerization site "B" are bared, (3) a process in which the produced fibrin monomers bind non-covalently each other right after another through an interaction between the polymerizing site "A" existing in the E region and the polymerizing site "a" existing in the D region, and (4) a process in which upon the resulting fibrin polymers factor XIII activated by thrombin (activated factor XIII) reacts and the adjacent D regions form cross-links (that is covalent bonds) through cross-linking reaction resulting in stable fibrins, and the conventional methods measure the coagulation parameters through monitoring the degree of the increase in turbidity or viscosity of the sample accompanied by progress of the above-mentioned process (4).

Here, as the types of the coagulation parameters measurable in these methods, blood coagulation times such as prothrombin time (PT) to inspect whether the extrinsic pathway of coagulation is normal or abnormal, activated partial thromboplastin time (APTT) to inspect whether the intrinsic pathway of coagulation is normal or abnormal; thrombotest and hepaplastin test to investigate whether vitamin K-dependent coagulation factors are normal or abnormal; the % activities of coagulation inhibitors such as Protein C, Protein S and the like; the plasma contents of each coagulation factor relating to the coagulation cascade reaction such as factor II, V, VII, VIII, IX, X, XI, XII and the like; and plasma levels of fibrinogen and the like can be mentioned.

In the above-mentioned conventional methods for measuring the coagulation parameters, however, because of the need to produce stable fibrin due to the principle for the measurements, it has been substantially impossible to use automated analyzers for the measurements. Accordingly, because the resulting stable fibrin will clot and firmly stick to a reaction vessel (such as a cuvette, cup and the like), and then it can not be removed without manual operations such as removal using a spatula, the reaction vessel can be used only once for the measurements of the coagulation parameters. Because of this reason, the reaction vessel after the measurement has to be disposed and thus the methods cannot be applicable to automated analyzers which repeatedly use the reaction vessels. Accordingly, under the current situation, only the measurements of the coagulation parameters are measured using an exclusive devise for blood coagulants independently of many other test items (the test items for which biochemical reagents and immunological reagents are used) which can be all measured in one automated analyzer.

Although some methods to solve the above-mentioned problems have been reported, none of them has been put to practical use. For example, Japanese Unexamined Patent Publication No. 7-255497 discloses a method wherein the coagulation parameters are measured when fibrin clotting process is forced to stay within the phase of fibrin polymer formation (where the fibrin monomers are precipitated as fibrin net) by adding an inhibitor of factor XIII to the reaction system, and after the measurements, the fibrin polymers are dissolved by addition of a solution to remove the affinity among the fibrin molecules. This method also indicates that used reaction vessels can be reused. As any of the inhibitors against factor XIII used in this methods is, however, a dangerous drug, safety must come into question. Moreover, whereas the said method requires the addition of a solution to remove the affinity among the fibrin molecules aiming at dissolving fibrin polymers, those specifically exemplified as the said solutions are strong acids such as hydrochloric acid which may corrode or damage the reaction vessel (such as a cell) and the measuring devise itself. In addition, as these solutions are added after completion of coagulation, a new line for addition of the solution is necessary to be established in the measuring devise, indicating a problem that an automated analyzer which has already used commonly can not be used as it is.

Still, no description is presented in the above-mentioned publication about reproducibility of the measured data, consistency with the conventional methods for measuring the coagulation parameters using multiple samples and the like, leaving credibility on these issues unclear.

As mentioned hereinbefore, to the best of the inventors' knowledge, no method for measuring the coagulation parameters, which is simple and applicable to existing automated analyzers has been described. Thus, the invention aims at development of a method for measuring the coagulation parameters, which is credible and applicable to existing automated analyzers.

SUMMARY OF THE INVENTION

Guided by an idea that the above-mentioned purpose can be achieved by measuring the coagulation parameters without generating fibrin clot (or stable fibrin) and then fibrin net in a reaction vessel, the inventors conducted a diligent investigation on a method which brings about a change in a physical value of the sample corresponding to the coagulation parameters without generating fibrin clot and fibrin net. As a result, it was found that by suppressing and inhibiting the formation of non-covalent bond among fibrin monomers which is catalyzed and produced by thrombin, and then avoiding the formation of fibrin clot and further fibrin net, a change in a physical value of the sample before the formation of fibrin net (i.e., fibrin polymers are deposited out)

shows an extremely close correlation to any type of the coagulation parameters.

Accordingly, the invention enables determination of the coagulation parameters in a fluid sample before the said sample to be tested completes clotting by utilizing the above-mentioned correlation.

Such an invention is a method for determining the coagulation parameters in a clotting system comprising fibrin clotting process accompanied by limited degradation of fibrinogen by thrombin, which comprises of;

A. a process to contact a fibrinogen-containing fluid sample to be tested with a blood coagulation reagent at the presence of a material which inhibits the formation of fibrin polymers from fibrin monomers in the aforementioned fibrin clotting process, B. a process to detect the change in a physical value of the said sample which changes is triggered by such a contact, and C. a process to evaluate the change in the physical amount detected as an indicator presenting a coagulation parameter.

Furthermore, this invention provides a kit to determine the coagulation parameters comprising of a material to inhibit the formation of fibrin polymers from fibrin monomers, a blood coagulation reagent, and optionally a standard sample which coagulation parameters are known, as a combination, all of which can be used in practicing the above-mentioned invention.

In the above-mentioned method of the invention, as a close correlation exists between the results obtained with the typical conventional methods for measuring the coagulation parameters and the changes in the physical amounts before deposition of fibrin monomers in the samples tested according to the procedure described hereinbefore, the coagulation parameters of the said sample can be determined by comparing the changes in the physical amounts obtained in the method of the invention from a standard sample which coagulation parameters are known with the changes in the physical value obtained in the method of the invention from the sample to be tested without clotting in the operating system.

DESCRIPTION OF THE PREFERRED EMBODIMENTS

Figure 1:
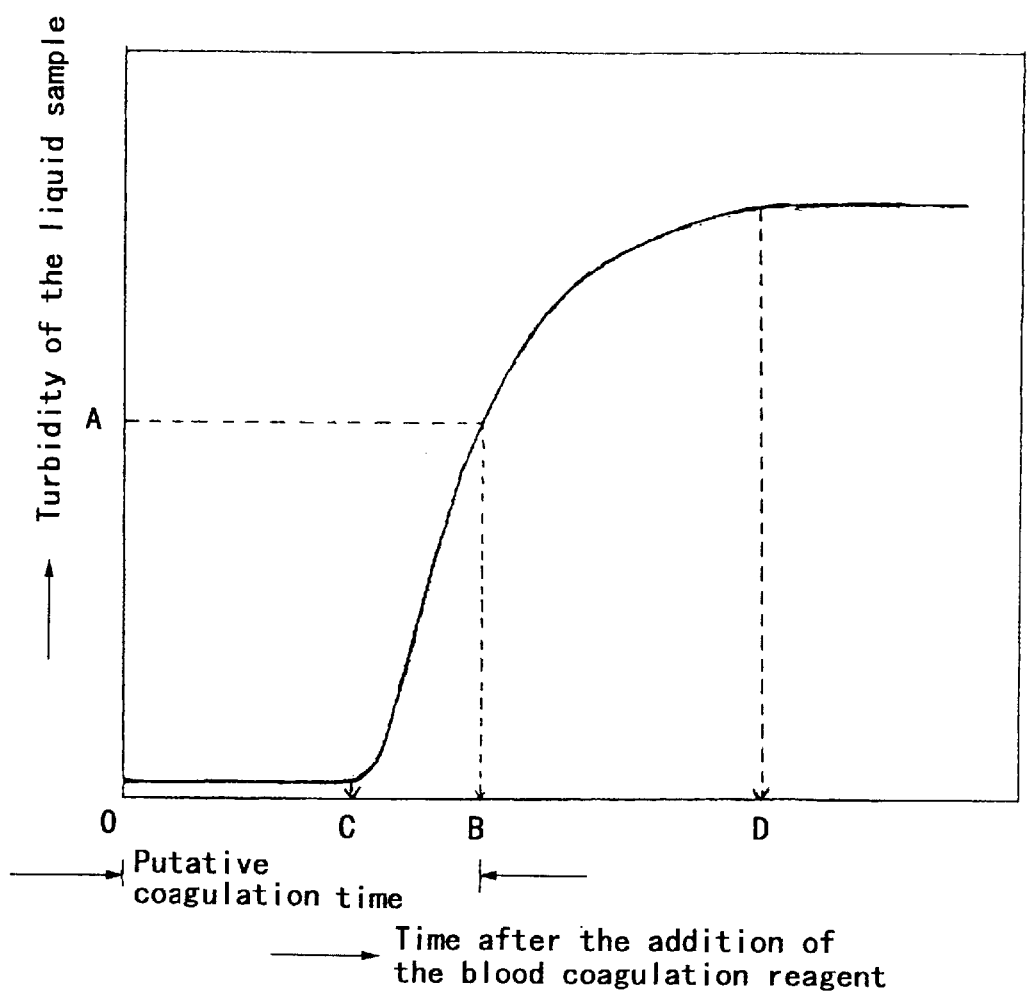
FIG. 1 is a typical example of a turbidity rise curve showing the changes in turbidity of a liquid sample occurred in contacting the liquid sample with a blood coagulation reagent at the presence of a coagulation inhibitor (which is specifically described hereinafter, and so forth on).

Despite the occurrence of the deposition of fibrin polymers (or fibrin net), the method of the invention can be conducted with intended effects as long as the deposition can be easily removed from the reaction vessel (for example, cuvette, cup and the like). However, considering convenience of the operation, detecting the degree of change in a physical value of the sample before the deposition of the said fibrin polymers is occurred is preferable.

Although it is not intended to be bound to theories, because of existence of for example an antibody against the fibrinogen E region or a material to inhibit the formation of fibrin polymers from fibrin monomers such as fibrin degradation product D dimers and the like (which is sometimes referred as to a coagulation inhibitor) in the invention, the formation of fibrin polymers from fibrin monomers is believed to be inhibited or delayed by 1) blockage of polymerization site "A" and/or "B" existing within the E region of a fibrin monomer, 2) steric hinderance caused by neutralization of the entire E region of a fibrin monomer, or 3) the combination thereof. However, whereas the formation of fibrin polymers is inhibited in this case, because a reaction between fibrin monomers and the above-mentioned coagulation inhibitor or a reaction between the said reaction product and fibrin monomers, or the like leads to some degree of the physical change correlating to a coagulation parameter such as a change in turbidity and the like in a liquid sample after the contact with a blood coagulation reagent, as a result of the detection of the said degree of the physical change, the above-mentioned purpose is believed to be achieved.

A sample in which the coagulation parameters can be determined according to the method of the invention may be naturally-occurred or artificial one as long as it is a sample which can bring about fibrin clotting process accompanied by limited degradation of fibrinogen by thrombin when contacted with a blood coagulation reagent. But normally, a liquid containing at least fibrinogen, wherein the liquid is the whole blood or plasma or a preparation thereof (for example, a concentrate, a diluent diluted with a buffer and the like) derived from a warm-blooded animal (for example, human, bovine, swine, sheep and the like) is to be a sample to be available to determination of the coagulation parameters according to the invention.

A material to inhibit or suppress the formation of fibrin polymers from fibrin monomers, which is used in the invention, is the one which can inhibit or suppress formation of fibrin polymers by interacting with fibrin monomers and may be any material as long as it answers the purpose of the invention independent of the species and origin. The term "inhibit" or "suppress" means an action in which fibrin monomers can make some physical change in a sample and which can completely or slightly hamper the formation of fibrin polymers to delay clotting or coagulation. However, such a material is preferably selected from a group consisting of peptides or proteins which can bind the E region of fibrin monomers and peptides or proteins which can bind the D region of fibrin monomers. As typical peptides or proteins which can bind the E region of fibrin monomers, antibodies against fibrinogen degradation product E or antibodies against fibrin degradation product E can be mentioned. Moreover, fibrin (or fibrinogen) degradation products, and more specifically fragments obtained by limited degradation of fibrin (or fibrinogen) by plasmin, which contain the D segment can also be preferably used as inhibitors for the said formation of fibrin polymers.

On the other hand, as the peptides or proteins which can bind the D region of fibrin monomers, monoclonal antibodies against polymerization site "a" and "b" existing within the D region of fibrin monomers, polyclonal antibodies against fibrinogen degradation product D (FgDP-D), polyclonal antibodies against fibrin degradation product D (FDP-D) and the like can be mentioned. Among them, polyclonal antibodies against fibrinogen degradation product D (FgDP-D) and polyclonal antibodies against fibrin degradation product D (FDP-D) can be suitably used, as they can affect throughout the D region of fibrin monomer.

As antibodies against the said fibrinogen E region, more specifically, monoclonal antibodies against polymerization site "A" and polymerization site "B" existing within the E region of fibrin monomers, polyclonal antibodies against fibrinogen degradation product E (FgDP-E), polyclonal antibodies against fibrin degradation product E (FDP-E) and the like can be mentioned. Among them, polyclonal antibodies directed against fibrinogen degradation product E (FgDP-E) and polyclonal antibodies directed against fibrin degradation product E (FDP-E) can be suitably used, as they can affect throughout the E region of fibrin monomer.

Moreover, the term "E region, D region, degradation fraction of fibrin or fibrinogen" and the like used in the invention or in this specification is used to mean what is described, for example, in Marder V. J., Francis C. W., and Doolittle R. F. (1982) Hemostasis and Thrombosis; Basic Principles and Clinical Practice, ed. R. W. Colman, J. Hirsh, V. J. Marder, E. W. Salzman, pp. 145–63. Philadelphia, Pa.: Lippincoff. For more details, see the list of publications described hereinafter.

The method for producing the antibodies against the said fibrinogen E region is not specifically defined and general methods which are widely known can be utilized. For example, a polyclonal antibody against fibrinogen degradation product E (FgDP-E) can be suitably generated by the following method.

Namely, at the first, with addition and reaction of plasmin which is a digestive enzyme for fibrinogen, to obtain fibrinogen degradation product, and then from purification of the said fibrinogen degradation product, fibrinogen degradation product E (FgDP-E) is obtained. In this case, in order to conduct a highly reliable determination of the coagulation parameters, it is preferable to remove contaminated proteins derived from the fibrinogen D region from the degradation product. Here, the removal of contaminated proteins derived from the fibrinogen D region can be confirmed with Western blot method and the like using an antibody against the fibrinogen D region. The above-mentioned purification method of FgDP-E can be conducted by at the first letting it pass through a hydrophobic carrier to remove phospholipids in the degraded material, and then by applying a hydrophobic chromatography to the resulting fractions.

Using the thus purified FgDP-E as an immunogen, it is possible to obtain a polyclonal antibody against fibrinogen degradation product E by immunizing a goat, a rabbit or the like using a well-known method to obtain an anti-serum against fibrinogen degradation product E, and then by applying ammonium sulfate precipitation method, an ion exchange chromatography e.g. ion exchange chromatography using DE-52 (manufactured by Whatman, Ltd.) as carrier and the like to the said anti-serum. Still, as antibodies directed against the fibrinogen E region are commercially available in general and are easily accessible, it is convenient to use such antibodies. For example, polyclonal antibodies against the fibrinogen E region are sold by Medical Biological Laboratories, in Japan, Enzyme Research Laboratories and the like.

Furthermore, the methods to generate antibodies directed against the said fibrinogen D region are not specifically defined and general methods which are widely known can be used. For example, a polyclonal antibody against fibrinogen degradation product D (FgDP-D) can be suitably generated by the following method.

Namely, at first, by addition and reaction of plasmin which is a digestive enzyme for fibrinogen, to obtain fibrinogen degradation product, and then from purification of the said fibrinogen degradation product, fibrinogen degradation product D (FgDP-D) is obtained. In this case, in order to conduct a highly reliable measurement of the coagulation parameters, it is preferable to remove contaminated proteins derived from the fibrinogen E region from the degradation product.

Here, the removal of contaminated proteins derived from the fibrinogen E region can be confirmed with Western blot method and the like using an antibody against the fibrinogen E region.

In the above-mentioned purification method of FgDP-D, at the first a gel filtration purification process is conducted to obtain fractions in which FgDP-D and FgDP-E coexist, and then the said fractions are subjected to a hydrophobic chromatography to obtain fractions in which FgDP-D is eluted. Lastly, this purification can be completed by applying an affinity chromatography in which the said fractions are to pass through an insoluble carrier on which an antibody against fibrinogen degradation material E is immobilized.

Using the thus purified FgDP-D as an immunogen, it is possible to obtain a polyclonal antibody against fibrinogen degradation product D by immunizing a goat, a rabbit or the like using a well-known method to obtain an anti-serum against fibrinogen degradation product D, and then by applying ammonium sulfate precipitation method, an ion exchange chromatography e.g. ion exchange chromatography using DE-52 (manufactured by Whatman, Ltd.) as carrier and the like to the said anti-serum. Still, as antibodies directed against fibrinogen D region are commercially available in general and are easily accessible, it is convenient to use such antibodies. For example, polyclonal antibodies against the fibrinogen D region are sold by Medical Biological Laboratories, in Japan, and the like.

Furthermore, as the peptides or proteins which can bind the above-mentioned E region of fibrin monomers, more specifically polymerization site "A" and/or polymerization site "B", peptides derived from the polymerizing site a existing within the fibrinogen D region, fibrinogen degradation product D monomers, fibrin degradation product D dimers, the said degradation product fractions containing D dimers and the like can be mentioned. Among them, it is suitable to use fibrin degradation product D dimer in terms of the strength of the above-mentioned inhibition effects.

Although the method for producing fibrin degradation product D dimer is not specifically defined, for example it can be produced by the following method. Namely, at first, by addition and reaction of thrombin to fibrinogen containing factor XIII to generate stable fibrin, then by addition and reaction of plasmin which is a digestive enzyme for the said stable fibrin to obtain fibrin degradation product, and finally from purification of the said fibrin degradation product, fibrin degradation product D dimer can be obtained. In the purification, in order to conduct a highly reliable determination of the coagulation parameters, it is preferable to remove contaminated proteins derived from the fibrinogen E region from the degradation product, and the removal can be confirmed with Western blot method and the like using an antibody against the fibrinogen E region. Specifically, at the first the degradation product is to pass through a hydrophobic carrier to remove phospholipids in the degradation product, then the pass-through fractions are subjected to a gel filtration to obtain fibrin degradation product D dimer fractions, and finally the resulting fractions are subjected to a hydrophobic chromatography to obtain purified fibrin degradation product D dimers.

In the invention, a material to inhibit the above-mentioned formation of fibrin polymers from fibrin monomers is used in combination with a blood coagulation reagent. As such blood coagulation reagents, at least one type(s) of reagent(s) selected from reagent containing materials with negative change on its surface (activator) and cephalin, reagent containing thrombin, reagent containing a variety of blood coagulation factors (for example, blood coagulation factors in the reagent are selected from a group consisting of factor II (prothrombin), factor III (tissue factor), factor IV (calcium ion), factor V (labile factor), factor VII, factor VIII (anti-hemophilic factor), factor IX, factor X, factor XI, factor XII (Hageman factor), factor XIII (fibrin stabilizing factor), prekallikrein and high molecular weight kininogen. The reagent contain one or more factor among those factor, whereas lack any of those factors), Protein C activating reagents, and optionally reagents which contains an inorganic salt or a buffering agent can be mentioned. The origin of the above-mentioned factors may be other than human. Typical reagents are commercially available and they may be used without adding other agent.

As typical coagulation parameters which can be determined according to the invention, prothrombin time (PT), activated partial thromboplastin time (APTT); fibrinogen concentration; thrombotest % activity; hepaplastin test % activity; Protein C % activity; Protein S % activity; content of blood coagulation factor II, factor V, factor VII or factor X; content of blood coagulation factor VIII, factor IX, factor XI, or factor XII, and the like can be mentioned.

As specific examples of combinations of a coagulation parameter to be determined and a commercially available blood coagulation reagent, Thromboplastin·C Plus (manufactured by Dade Diagnostics of P.P. Inc.) as a reagent for measuring prothrombin time (PT), Dade Actin Activated Cephaloplastin Reagent·ATCC (manufactured by Dade Diagnostics of P.P. Inc.) as a reagent for measuring activated partial thromboplastin time (APTT), Dade Fibrinogen Determination Reagent (manufactured by Dade Diagnostics of P.P. Inc.) as a reagent for measuring fibrinogen, Compound Factor-T Kokusai (manufactured by International Reagents Corp.) as a reagent for measuring thrombotest and the like can be mentioned.

Generally, prothrombin time (PT) for a healthy human falls within the range of 11 through 13 seconds, and if it surpasses this range, deficiencies of factor II, factor V, factor VII, or factor X, hepatopathy, vitamin K deficiency and the like are suspected. Activated partial thromboplastin time (APTT) for a healthy human falls within the range of 25 through 35 seconds, and if it surpasses this range, hemophilia, hepatobiliary diseases and the like are suspected. The other coagulation parameters have been related to some diseases. Accordingly, this invention is useful for diagnosis of a variety of diseases.

Samples to be tested according to the invention are treated in a condition in which pH is adjusted with buffering agent, if needed. Here as buffering agent which can be generally used, a series of compounds called GOOD buffering reagents such as 2-[4-(2-hydroxyethyl)-1-piperadinyl] ethansulphonic acid, 3- [4-(2-hydroxyethyl)-1-piperadinyl] propansulphonic acid, 2-morpholinoethansulphonic acid and the like as well as tris(hydroxymethyl)amino-methane and the like can be mentioned. Although the concentration of a buffering agent is not specifically defined as long as it can keep pH constant even after contact with a blood coagulation reagent and it does not inhibit the blood coagulation reaction significantly, generally the concentration falling within the range of 5 though 20 mM is suitable. Moreover, generally pH range of 6 through 9 is suitable for the buffer solutions.

In addition, to the above-mentioned sample, an inorganic salt such as sodium chloride and the like can be added in order to adjust the ion strength. Ion strength is known to affect the rate of blood coagulation reaction. As the above-mentioned concentrations of buffering agents relate to ion strength, the amount of an inorganic salt to be added may be decided properly in accordance with the types and other properties of the buffering agent to be used, whereas generally the sum of the concentrations of the buffering agent and the inorganic solution is suitably to fall within a range of 50 through 900 mM. The above-mentioned sample may be subjected to further processings as long as they can meet the objectives of the invention. When exemplified the whole blood or plasma, a venous blood is taken in blood sample tube to which sodium citrate was added in advance, and then blood sample tube is centrifuged at 3000 rpm for 10 min and the resulting supernatant can be used as the plasma to be tested. Shelf-life of the thus obtained plasma sample is usually 6 hours at room temperature and approximately 10 days at −20° C.

When conducting a method according to the invention, a process to contact a liquid sample with a blood coagulation reagent in the presence of a material which inhibits the formation of fibrin polymers (which is referred as to a coagulation inhibitor hereinafter) is not specifically defined, thus any of the following procedures can be applied; 1) a procedure in which a fluid sample and a coagulation inhibitor are mixed in advance, and then the said mixture is to contact with a blood coagulation reagent, 2) a procedure in which a coagulation inhibitor and a blood coagulation reagent are mixed in advance, and then the said mixture is to contact with a fluid sample, or 3) a procedure in which all of the three substances are mixed at once. Specifically, a procedure in which a aliquot of the solution containing a liquid sample and a coagulation inhibitor is taken into a reaction vessel using a micropipette, and then, a blood coagulation reagent is added using a multipipettor and the like to make it contacted with the mixture, a procedure in which a fluid (or liquid) sample which has been diluted with a solution containing a coagulation inhibitor in advance is placed in a measurement cell, and then a blood coagulation reagent is added to make it contacted with the sample or to incubate the mixture, a procedure in which a liquid sample is placed in a measurement cell, and using a blood coagulation reagent which has mixed in advance with a coagulation inhibitor as the blood coagulation reagent which used regularly, the liquid sample make contact with the blood coagulation reagent by operating a popular automated analyzer, or the like are suitably adopted. Now, the term "a fluid or liquid sample" as used in this specification means a sample free from solid matters which adversely affect the detection system according to the invention.

A contact method using an automated analyzer is simply outlined hereinafter.

A general automated analyzer which is widely used is composed of two reagent-addition systems and its measurement cell is always kept warm at around 37° C.

And, the measurement by an automated analyzer can be conducted according to the following procedures.

Firstly, the first reagent (R1) is fractionated into a measurement cell by R1 probe. Then, to the measurement cell containing the first reagent, a liquid sample is added by a sample probe followed by stirring in an installed stirring mechanism. Then, to the said measurement cell, the second reagent (R2) is added by R2 probe followed by stirring in an installed stirring mechanism. Then, turbidity (absorbance) after the addition of the second reagent and stirring the mixture is measured intermittently, usually once in approximately 20 seconds. Finally, after completion of the measurement for about 6 minutes, as the last stage of the measuring process, the reaction solution is disposed from the measurement cell through a nozzle of a washing mechanism.

As the contact procedures conducted in an automated analyzer illustrated by exemplifying a case of prothrombin time (PT) measuring system, a procedure in which the mixture of a coagulation inhibitor and tissue thromboplastin (calcium free) as the above-mentioned first reagent, and a calcium chloride solution as the above-mentioned second reagent (R2) is set in a automated analyzer to let them contact, a procedure in which the coagulation inhibitor as the above-mentioned first reagent (R1) and the PT reagent solution as the above-mentioned second reagent (R2) are set in an automated analyzer to let them contact and the like can be mentioned.

As the reaction vessels, a reaction vessel used in a measuring device which can monitor the change in a certain physical value of the sample, or a reaction vessel equipped with an automated analyzed can be used without any limitations. For example, measurement cells made of plastics which are equipped with widely used automated analyzers, measurement cells made of glass and the like can be mentioned. Preferably, a plastics vessel such as a plastics measurement cell or the like which induces less absorption and activation of blood coagulation factors can be used. Moreover, the temperature for the contact or incubation is not specifically limited, and these processes may be conducted at a temperature that falls within a range of settings available for a measuring device, whereas it is preferable to make the contact at a temperature of around 37° C. at which the coagulation reactions proceed smoothly. In addition, no specific limitation is set for the contact conditions. For example, a condition for the contact in which after the addition of a blood coagulation reagent with a mutipipette or the like, the resultant is stirred and mixed using a built-in stirring mechanism in the measuring device or a stirring device can be mentioned. Also the contact time is not specifically limited, and the contact time depends on the setting and the maximum of the monitoring time of a measuring device which can monitor the change in a certain physical value of the sample. For example, in widely used automated analyzers, the contact times up to approximately 12 through 20 minutes are available although the contact time depends on the type of the device.

At this time, the amount of coagulation inhibitors to be used is not specifically limited, and it may be decided depending on the types and amounts of the blood coagulation samples to be tested, as well as on the types of coagulation parameters to be measured, whereas generally it is preferable to use the amount which falls within a range of 1 through 50 mg / ml as the concentration in a solution (which is referred as to "reaction system" hereinafter) where a liquid sample and a blood coagulation reagent have made a contact.

For example, when prothrombin time (PT) is measured using fibrin degradation product D dimers as the coagulation inhibitor, in order to obtain a sufficient coagulation inhibition effect, it is preferable to fibrin degradation product D dimers is coexisted in an amount of seven times or more as much as the final concentration in molar ratio of fibrinogen derived from the liquid sample in the reaction system. As an example, when the final concentration of fibrinogen in the reaction system is 400 mg/dl, it is preferable that fibrin degradation product D dimers is coexisted in the reaction system at a concentration of 16 mg/ml or higher.

Moreover, for example, when prothrombin time (PT) is measured using a goat polyclonal antibody against fibrinogen degradation product E (manufactured by Medical Biological Laboratories, in Japan) as an antibody against fibrinogen E region, which is a coagulation inhibitor, the said antibody is preferably used in an amount of approximately 1 mg through 10 mg as the antibody amount calculated based on Becker's test, or in an amount of approximately 9 times through 90 times as much as the final concentration in molar ratio of fibrinogen derived from the liquid sample in the reaction system as the antibody amount calculated based on the protein amount.

Furthermore, for example, when prothrombin time (PT) is measured using a rabbit polyclonal antibody against fibrinogen degradation product D (manufactured by Medical Biological Laboratories, in Japan) as an antibody directed against the fibrinogen D region, which is the coagulation inhibitor, the said antibody is preferably used in an amount of approximately 1 mg through 10 mg as the antibody amount calculated based on Becker's test, or in an amount of approximately 3 times through 30 times as much as the final concentration in molar ratio of fibrinogen derived from the liquid sample in the reaction system as the antibody amount calculated based on the protein amount.

In the invention, the coagulation parameters are determined by detecting the degree of a physical change of a liquid sample which changes after the contact of the above-mentioned liquid sample and a blood coagulation reagent. Now, the degree of the physical change of the liquid sample to be detected is what changes by the above-mentioned contact and is not specifically limited as long as the degree of the change has anyhow a correlation with the coagulation parameters. As such physical value, turbidity as mentioned earlier (including absorbance), viscosity, permittivity and the like can mentioned, whereas it is preferable to detect turbidity (or absorbance) due to easiness of the detection.

A case using the turbidity (or absorbance) as the physical value whose change to be detected is further illustrated in detail hereinafter.

Turbidity (or absorbance) of a liquid sample can be easily monitored optically, and the detection of the degree of turbidity change can be conducted easily using commercially available devises such as STAT IMUNO SYSTEM Quick Turbo II (manufactured by A & T Corp.), an automated analyzer Multiple Chemistry Unit 502X (manufactured by A & T Corp.), an automated analyzer Automatic Analyzer 7070 (manufactured by Hitachi Ltd.) and the like.

An example to detect the degree of turbidity change using STAT IMUNO SYSTEM Quick Turbo II is shown hereinafter.

At the first, after taking a liquid sample and a coagulation inhibitor into a measurement cell, the mixture is placed in a heating section and heated for a certain time. Then, the measurement cell is set in a measuring section, and a blood coagulation reagent is added in a certain amount. At the same time as the addition, the mixture is automatically stirred, and immediately after the stirring the turbidity changes are automatically measured once every second. Then, by the measurements the degree of the sequential turbidity change are shown.

Also as an example to detect the degree of turbidity change using an automated analyzer, a procedure in which by setting the coagulation inhibitor as the first reagent (R1) and the blood coagulation reagent as the above-mentioned second reagent (R2), the degree of turbidity change is automatically detected and the like can be mentioned.

In the case of the turbidity measurements using the automated analyzer Multiple Chemistry Unit 502X, two wave lengths among 16 wave lengths existing between 340 and 795 nm can be selected as the wave lengths for the measurements. The selected two wave lengths can be simultaneously measured through the intermittent measurements conducted once in approximately 20 seconds. When R1 and R2 are set in the above-mentioned arrangement, the turbidity measurements can be conducted for approximately five minutes. Then from the measurements, the degree of sequential turbidity change can be shown.

When the turbidity measurements are conducted using the automated analyzer Automatic Analyzer 7070, two wave lengths among 12 wave lengths existing between 340 and 800 nm can be selected as the wave lengths for the measurements.

The selected two wave lengths can be simultaneously used with the intermittent measurement conducted once in approximately 20 seconds. In other cases, the degree of serial turbidity change can be shown in almost the same way as the case of the automated analyzer Multiple Chemistry Unit 502X.

Furthermore, the methods for the measurement or detection described above can apply to systems using chromogenic substrates for thrombin (such as S-2238 (manufactured by Chromogenix AB) and the like). The system utilizing a chromogenic substrate for thrombin means a procedure taking advantage of what the amount of thrombin generated from the above-mentioned cascade reaction and the amount of a chromogenic substance (in the case of S-2238, it will be p-nitroaniline) freed from chromogenic substrate for thrombin as a result that the said thrombin acts on the said chromogenic substrate are proportionally correlated. Such a procedure can be especially suitable for the case in which an antibody against fibrinogen degradation product D monomers or an antibody against fibrin degradation product D dimers is used as the coagulation inhibitor. However, when a chromogenic substrate for thrombin is used, the quantitative determination of fibrinogen among the above-mentioned coagulation parameters is not feasible.

An example of the measurement using S-2238 as the above-mentioned chromogenic substrate for thrombin and STAT IMUNO SYSTEM Quick Turbo II is shown hereinafter.

At the first, after taking a liquid sample and a coagulation inhibitor into a measurement cell, they are heated in the heating section for a certain time. Then, the measuring cell is set in the measuring section and the mixture of a blood coagulation reagent and an aqueous solution of S-2288 is added in a certain amount. As soon as the addition, they are automatically stirred, and immediately after the stirring, absorbance changes at wave length 405 nm are automatically measured once every second. Then, from the measurements, sequential changes in the absorbance can be shown.

Also as an example of the measurement using an automated analyzer, a procedure in which by setting the coagulation inhibitor as the first reagent (R1), and the mixture of the blood coagulation reagent and an aqueous solution of S-2283 as the above-mentioned second reagent (R2), the degree of absorbance changes are automatically measured and the like can be mentioned. In this case, the completely same procedure as the previous one can apply except that 405 nm is selected as the wave length to be measured.

In this invention, by detecting according to the method of the invention the degree of change in a physical value of a liquid sample (a standard sample) which coagulation parameters have already measured in the conventional method and known to provide a reference to a test sample, and then by obtaining the correlation between both the degree of change in physical value of the sample and coagulation parameters samples in advance (for example, by making a calibration curve), the coagulation parameter of the test sample can be determined from the degree of change in physical value of the sample actually measured in accordance with the said correlation (or calibration curve).

By exemplifying a case where the degree of change in physical value to be detected is those of turbidity changes, a procedure to determine a coagulation parameter from the degree of turbidity changes is illustrated in detail hereinafter.

When contacting a liquid sample and a blood coagulation reagent at the presence of a coagulation inhibitor, the turbidity of the liquid sample after the contact changes as shown in the turbidity rise curve is shown in FIG. 1. Still, when an automated analyzer is used to detect turbidity, whereas the automated analyzer will measure turbidity only once in some ten seconds (for example, in the case of the above-mentioned automated analyzer Multiple Chemistry Unit 502X, it measures only once in approximately 18 seconds), by measuring the turbidities of the shorter and longer wave lengths both at once, and by carrying out a statistical operation and calculation from the individual turbidity rise profiles, it is possible to obtain a turbidity rise curve as shown in FIG. 1. Using the turbidity rise curve in the said FIG. 1, it is possible to determine the coagulation parameters of the liquid sample, specifically the coagulation factors such as coagulation time, fibrinogen concentration, thrombotest % activity and the like.

Figure 8:
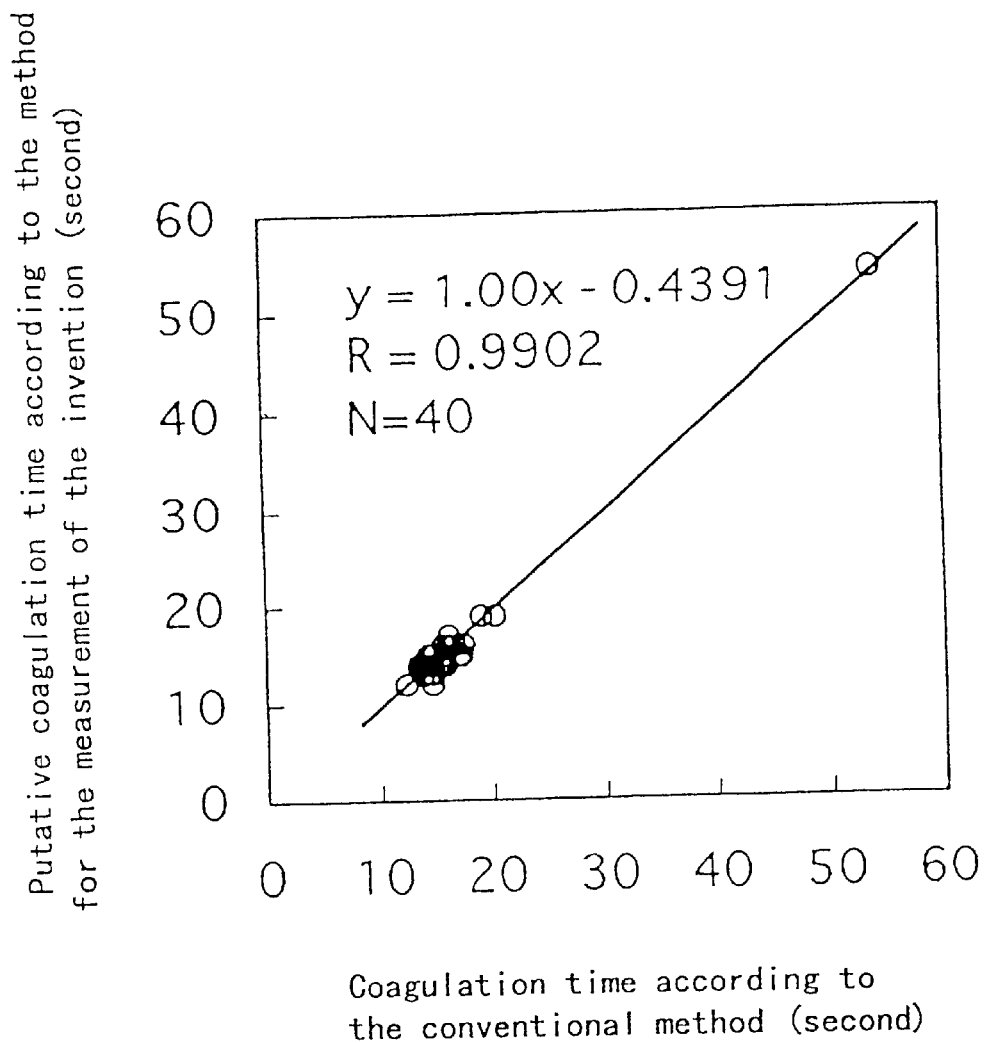
FIG. 8 is a correlation diagram between the results obtained from the PT measurements using the anti-FgDP-E antibody as the coagulation inhibitor in the method of the invention and the results obtained from a conventional method.

Accordingly in FIG. 1, a point where the turbidity of the liquid sample reaches a certain value, A, which is determined arbitrarily in advance, is defined as the endpoint (B) where the coagulation reaction is supposed to finish and the time period between the addition of the blood coagulation reagent and the endpoint is defined as the putative coagulation time. This putative coagulation time, which indicates the degree of turbidity change, has a superior correlation with the coagulation time obtained according to the conventional method as shown in FIG. 8. Accordingly, with conversion the putative coagulation time into coagulation time through FIG. 8, the coagulation time can be obtained from the putative coagulation time.

Here, because of the superior correlation with the conventional method, it is preferable to make the first-degree differential curve for the turbidity rise curve in FIG. 1 and then to define the turbidity at the point corresponding to the peak of the said first-degree differential curve as point A.

Moreover, not only putative coagulation times but also degrees of turbidity increase per unit time (that is so-called slop) show a superior correlation with coagulation times obtained in the conventional method.

In this case, the degree of turbidity increase per unit time shows a reverse correlation with the coagulation time obtained in the conventional method. The reverse correlation means that the larger the degree of turbidity increase per unit time is, the shorter the coagulation time obtained according to the conventional method becomes. The choice of unit time in this context is not specifically limited, but because of the superior correlation, an arbitrary range within the time period from the starting time of turbidity increase (point C) to the time (point D) when the turbidity increase is leveled off may be selected. The time period from the starting time of turbidity increase (point C) to an arbitrary time can be preferably used. Here, the degree of turbidity increase per unit time can be referred as to A/(B−C) [unit; absorbance/time] when exemplified using FIG. 1.

Figure 2:
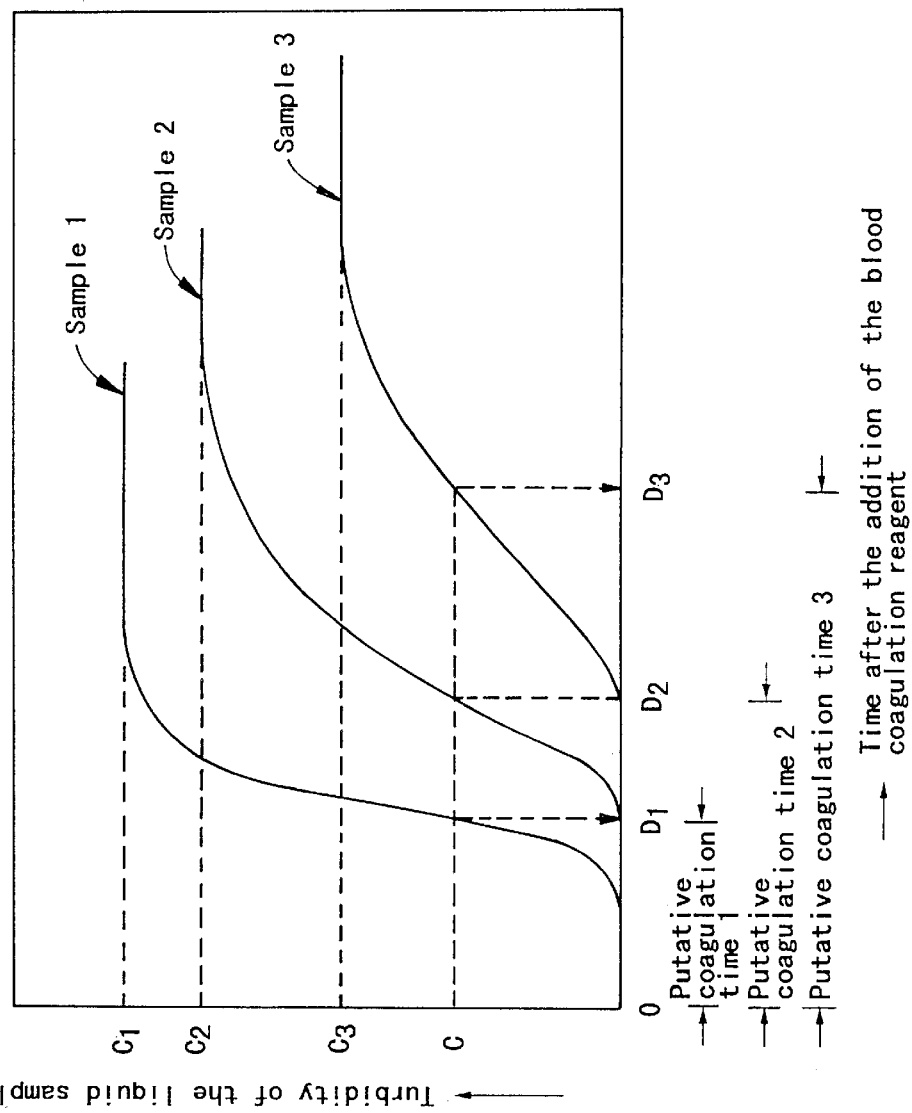
FIG. 2 is a schematic diagram illustrating a method to measure three samples with different fibrinogen concentrations in the method of the invention and then to obtain the putative clotting times from the resulting turbidity rise curves.
Figure 3:
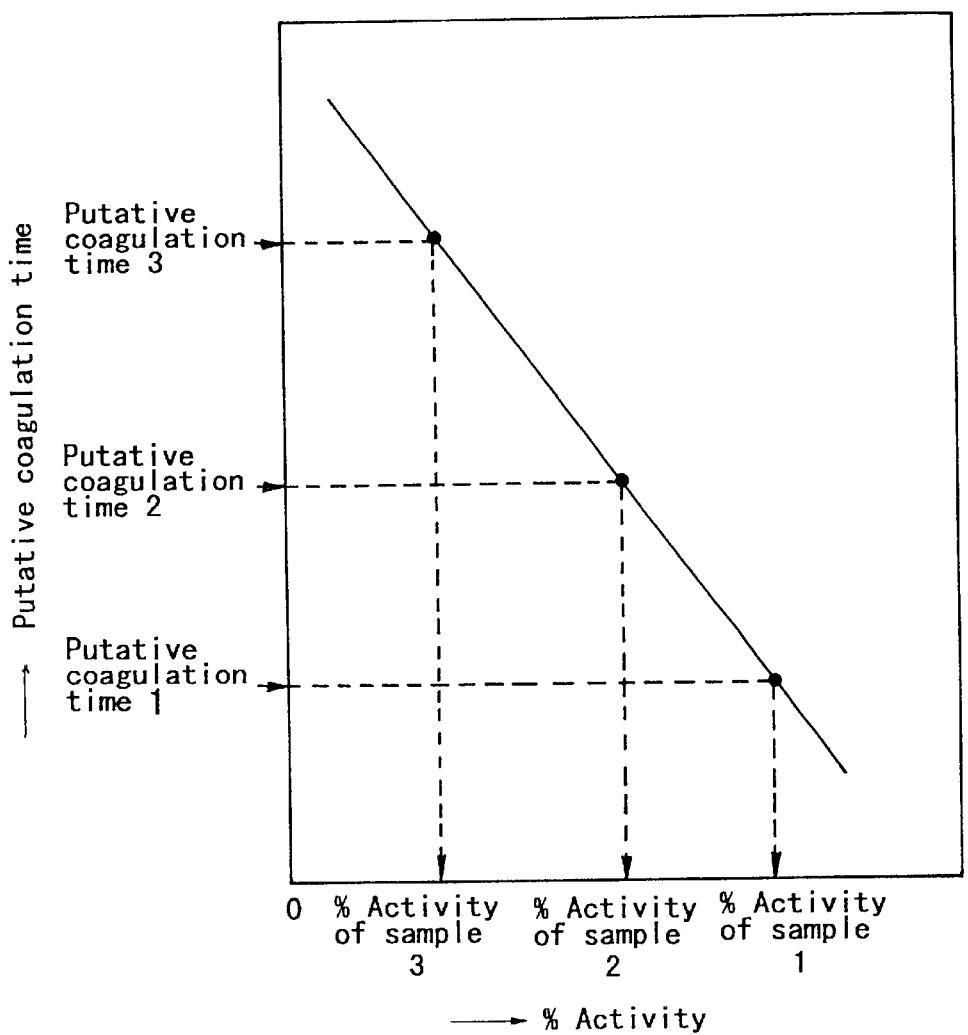
FIG. 3 is a calibration curve for the putative clotting times obtained by measuring the three samples which % activities are known in the method of the invention and % activities.

In addition, when determining fibrinogen concentration and thrombotest % activity, by obtaining a curve such as shown in FIG. 2 through the measurements of turbidity of plural of samples (sample 1, 2 and 3) whose fibrinogen concentrations and thrombotest % activities are known, by plotting the putative coagulation time ($D_1$, $D_2$, and $D_3$) corresponding to an arbitrary turbidity C which has been defined in advance for the said individual curves in FIG. 2 to make calibration curves such as shown in FIG. 3, and then by using the said calibration curves, fibrinogen concentrations and thrombotest % activities can be determined from the putative coagulation time.

Here, by plotting the saturation turbidities (for example, $C_1$, $C_2$ and $C_3$ in FIG. 2) corresponding to fibrinogen concentrations in the individual samples to make calibration curves, and by utilizing the said calibration curves, fibrinogen concentrations can be also determined.

In the invention, as the coagulation parameters can be detected from the degree of change in physical quantity on a sample before the formation of fibrin net, it is possible to utilize the automated analyzers which have never been available to determine the coagulation parameters. Moreover, the method for determining the coagulation parameters of the invention is not only applicable to existing automated analyzers as they are because of the safe and convenient operations, but also provides highly reliable results from the measurements.

In this manner, the invention is to allow the measurements of the coagulation parameters (coagulation tests) for which a single automated analyzer has not been shared with other testing items (that is, testing items conducted by using biochemical reagents and immunological reagents) to be conducted, like other testing items, in a single device which is also utilized for the measurements of other testing items, as well as is to largely contribute to increase the testing efficiency and to reduce the testing costs.

The invention is illustrated referring examples hereinafter, whereas it is not intended that the invention is limited to the said examples.

Here, as coagulation inhibitors for the individual examples, fibrin degradation product D dimer (which is sometimes abbreviated as "DD" hereinafter) and the goat polyclonal anti-FgDP-E antibody (which is sometimes abbreviated as "anti-FgDP-E antibody" hereinafter) manufactured by Medical Biological Laboratories, in Japan, which is an antibody against fibrinogen degradation product E were used. The method to make DD as well as inhibitory effects of DD and the anti-FgDP-E antibody are illustrated hereinafter.

(The Method to Make DD (or D Dimer))

DD was made using the individual buffer solutions described below and according to the procedures illustrated below.

Buffer A: 50 mM Tris-HCl buffer solution (pH 7.6) containing 0.15 M NaCl, 18 mM $CaCl_2.2H_2O$ and 0.01% $NaN_3$.

Buffer B: 10 mM Tris-HCl buffer solution (pH 7.6) containing 0.4 M ammonium sulfate, 2 mM ε-aminocaproic acid, 1 mM $NaN_3$.

Buffer C: 20 mM Tris-HCl buffer solution (pH 7.6) containing 0.15 M NaCl, 2 mM ε-aminocaproic acid, 1 mM $NaN_3$.

Buffer D: 20 mM Tris-HCl buffer solution (pH 7.6) containing 1 M ammonium sulfate, 2 mM ε-aminocaproic acid, 1 mM $NaN_3$.

Buffer E: 20 mM Tris-HCl buffer solution (pH 7.6) containing 2 mM ε-aminocaproic acid, 1 mM $NaN_3$.

At the first, ten sets of 50-ml centrifugation tubes (manufactured by Iwaki Glass Inc.) to which 10 ml of Buffer A each was added were prepared. To all of the ten sets of above-mentioned centrifugation tubes, 150 mg each of Human Fibrinogen Grade L (manufactured by American Diagnostica) was added and suspended. Then, a 95 μl of thrombin solution (manufactured by Calbiochem-Novabiochem International, Inc.) resolved in Buffer A in a concentration of 100 unit/ml was added to each of the above-mentioned tubes and mixed, and the mixture was allowed to stand in TAIYO INCUBATOR M-100N (manufactured by TAITEC Corp.) at 37° C. for two hours for incubation, resulting in stable fibrin. After two hours, a cut was made in the stable fibrin with a spatula and then 100 μl of plasmin solution (manufactured by Wako Pure Chemical Industries Ltd.; 2.06 mg protein/ml) was added to each tube followed by shaking and incubation in TAIYO INCUBATOR M-100N (manufactured by TAITEC Corp.) at 37° C. for twelve hours. After the reaction, 200 μl of aprotinin (manufactured by Wako Pure Chemical Industries Ltd.; 2 mg aprotinin/5 ml Buffer A) solution was added to each degradation product solution to cease the plasmin digestion reaction, and then by collecting the said plasmin digest, 100 ml of the fibrin degradation product solution was obtained.

A hundred ml of the said fibrin degradation product was applied onto a column which was filled with Phenyl-Toyopearl (manufactured by TOSOH Corp.) which had been equilibrated with Buffer B, and after then, by eluting 300 ml of Buffer B and collecting the pass-through fractions, phospholipids in the degradation product were removed. Here, the condition used was that 2 cm of the inner diameter of the column, 15 cm of the column length, 20 ml/hr of the flow rate and 40 ml of the volume of Phenyl Toyopearl.

Four hundred ml of the obtained pass-through fractions was subjected to ultrafiltration using an ultrafiltration membrane UP-20 and an ultrafiltration device UHP-90 (both are manufactured by ADVANTEC TOYO KAISHA Ltd.) to concentrate it to 20 ml, and the said concentrate was placed in a dialysis membrane (manufactured by Wako Pure Chemical Industries Ltd.) and dialyzed against Buffer C for two hours, then this dialysis procedure was repeated once. The obtained 20 ml of dialysate was applied onto Sephacryl S-300 (manufactured by Pharmacia) which had been equilibrated with Buffer C to conduct purification according to a gel filtration method. Here, the purification was conducted using a column with the inner diameter of the column of 4.1 cm and the column length of 120 cm, the flow rate of 32.5 ml/hr (2.5 ml/cm$^2$/hr), the volume of Sephacryl S-300 of 1600 ml, and the volume of each collected fraction of 5 ml. By measuring $A_{280}$ (absorbance at 280 nm) of one of each five fractions obtained in the said purification procedure, the elution profile was made and after dialysis of the fractions in which proteins were eluted, the fractions in which DD (190 kd) was eluted were found by applying the dialyzate to non-reduced SDS-page.

The above-mentioned fractions in which DD was eluted were collected (100 ml), the said collected fraction was placed in a dialysis membrane (manufactured by Wako Pure Chemical Industries Ltd.) and dialyzed against Buffer D for two hours, and this dialysis procedure was repeated once again. The resulting dialyzate was applied onto Butyl-Toyopearl (manufactured by TOSOH Corp.) which had been equilibrated with Buffer D to conduct the purification procedure with a hydrophobic chromatography. The purification condition used at this time was as follows: 2 cm of the inner diameter of the column, 15 cm of the column length, 20 ml/hr of the flow rate, 40 ml of the total volume of Buthyl-Toyopearl, 4 ml of the collected fraction volume and elution with a reverse linear gradient of ammonium sulfate concentration from Buffer D (500 ml) to Buffer E (500 ml).

By measuring $A_{280}$ (absorbance at 280 nm) of one of each five fractions, the elution profile was made, and after dialysis of the fractions in which proteins were eluted, the fractions in which DD (190 kd) was eluted were found by applying the dialyzate to non-reduced SDS-page. By collecting the said fractions, 400 mg of a DD purified fraction was obtained.

(Fibrin Coagulation Inhibitory Effect of DD)

The inhibitory effect of DD on the fibrin polymer formation was studied by TP measurement. As the PT measuring reagent, a commercially available reagent called "Thromboplastin C Plus" (manufactured by Dade Diagnostics of P.P. Inc.) was used. This PT measuring reagent was used in the concentration twice as much as that used regularly by regenerating the lyophilized product of the reagent with a half of the regular volume of distilled water.

The DD solution to be added was prepared from a 90 μM DD concentrated solution which was prepared by concentrating the purified fraction of DD finally obtained in the above-mentioned procedure with ultrafiltration, and then by placing the concentrated solution into a dialysis membrane and dialyzing it against a 30 mM HEPES buffer solution (manufactured by Dojindo Laboratories; pH 7.4). By using the said concentrated solution and the above-mentioned 30 mM HEPES buffer solution, six DD solutions with 18, 22, 30, 45, 60 and 90 μM of the DD concentrations were made.

As liquid samples, "Dade Ci-Trol Coagulation Control Level I" and "Dade Ci-Trol Coagulation Control Level II" both of which are commercially available control plasma products (both are manufactured by Dade Diagnostics of P.P. Inc.) were used. Here, Dade Ci-Trol Coagulation Control Level I is a control plasma product made of normal plasma derived from normal individuals and Dade Ci-Trol Coagulation Control Level II is a control plasma product made of moderately abnormal plasma. In addition, the concentrations of fibrinogen in the above-mentioned control plasma were 8 μM and 9 μM, respectively (the observed values measured using a device; KC-10A (manufactured by Amelung GmbH, Lemgo), and an reagent; Dade Fibrinogen Determination Reagents (manufactured by Dade Diagnostics of P.P. Inc.)). Furthermore, the molar ratios of DD compared to fibrinogen (abbreviated as Fib hereinafter) when using the above-mentioned two types of control plasma products and the above-mentioned DD solution are shown in Table 1.

TABLE 1

| | | | | | | |
|---|---|---|---|---|---|---|
| The concentration of DD in the solution of the inhibitor, DD, prepared (μM) | 18.0 | 22.0 | 30.0 | 45.0 | 60.0 | 90.0 |
| The molar ratio of the DD/Fib when Dade Ci-trol Coagulation Control Level I is used. | 2.2 | 2.8 | 3.8 | 5.6 | 7.5 | 11.3 |
| The molar ratio of the DD/Fib when Dade Ci-trol Coagulation Control Level II is used. | 2.0 | 2.4 | 3.3 | 5.0 | 6.7 | 10.0 |

Evaluation of the inhibitory effect was conducted using KC-10A (manufactured by Amelung GmbH, Lemgo).

The measurements were conducted as follows. In seven KC-10A sample cups, steal balls were placed and to each of the said sample cups, 100 μl of Dade Ci-Trol Coagulation Control Level I plasma product was added with a micropipette. After then, to six out of the seven sample cups, 100 μl of the DD solution with different DD concentrations were added and mixed, respectively. And to the remaining one sample cup, 100 μl of a 30 mM HEPES buffer solution was added as a control.

The seven sample cups were transferred to the measuring section and heated at 37° C. for three minutes. Finally, 100 μl of the above-mentioned PT reagent was added and the coagulation time, that is the time period until fibrin clot occurred was measured. The each difference between the coagulation time obtained from the case in which the each DD solution was added and the coagulation time obtained from the control was calculated (this is abbreviated as the degree of coagulation time extension hereinafter). By plotting the molar ratio of the DD/Fib on the X axis and the degree of coagulation time extension on the Y axis, the effect of the DD addition was shown.

Here, the same procedures were conducted for the cases using Dade Ci-Trol Coagulation Control Level II.

Figure 4:
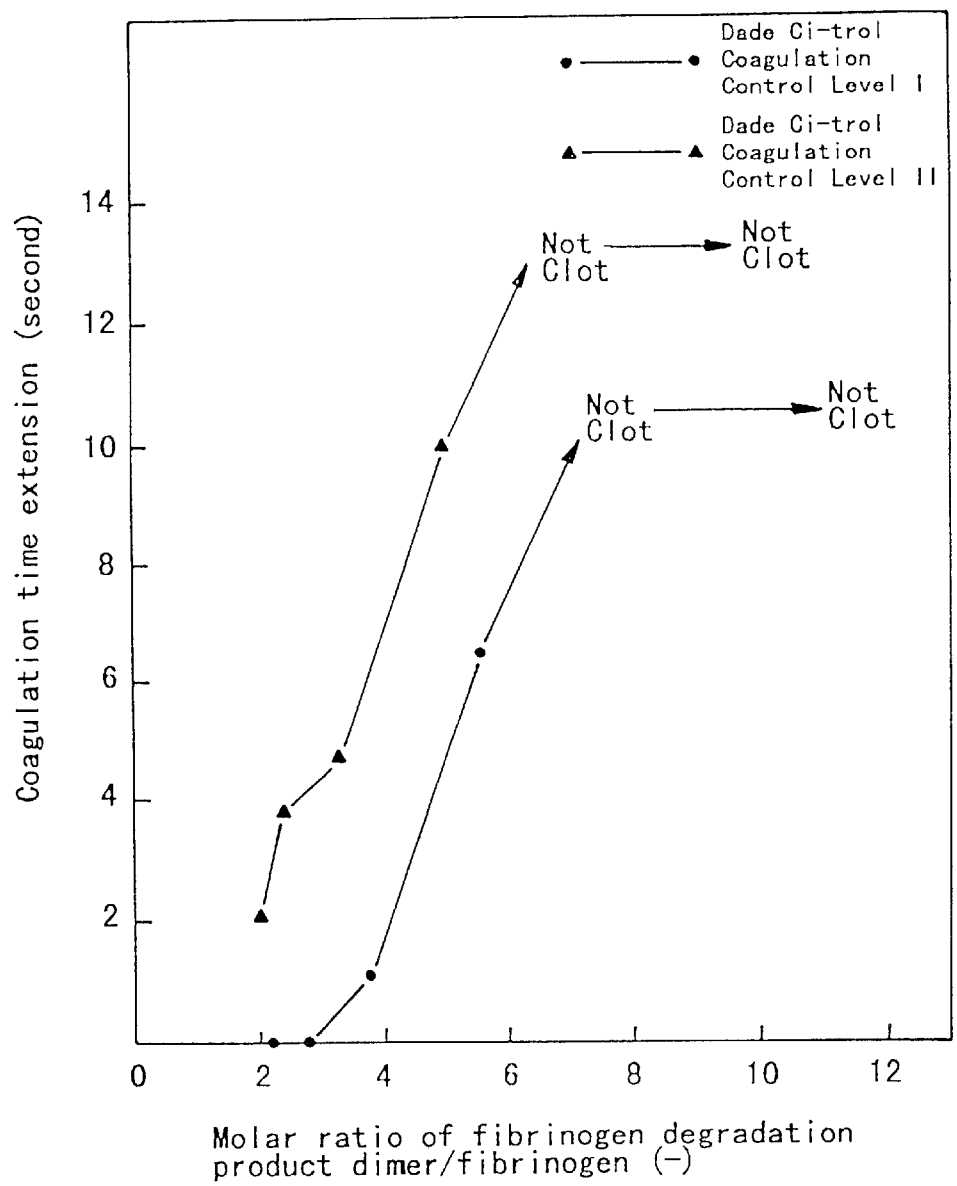
FIG. 4 shows coagulation inhibitory effects of fibrin degradation product D dimers.

The result is shown in FIG. 4. In FIG. 4, the cases where no coagulation occurred were represented with "NOT CLOT". As known from FIG. 4, coagulation was shown to begin to be avoided from the DD/Fib molar ratio of 7.5 with Dade Ci-Trol Coagulation Control Level I and 6.7 with Dade Ci-Trol Coagulation Control Level II. From this result, coagulation inhibitory effect of DD was clearly shown. And, the reaction completion product contained in the sample cup in the case that coagulation was avoided easily flowed out from the vessel by only turning the cup upside down.

(Fibrin Coagulation Inhibitory Effect of Anti-FgDP-E Antibody)

At the first, ten sets of Centricon-10 units (manufactured by Amicon Inc., cut-off molecular weight 10,000, as a ultrafiltration device) into which 2 ml of the anti-FgDP-E antibody solution each was placed were prepared. The antibody solution was concentrated by centrifuging Centricon-10 (at 3,000 rpm for 120 minutes). Then, the concentrated antibody solution was placed into a dialysis membrane (manufactured by Wako Pure Chemical Industries Ltd.) and dialyzed against a buffer solution (the composition: 30 mM HEPES buffer solution containing 350 mM sodium chloride, pH 7.4) for two hours to obtain a solution of the anti-FgDP-E which was to used for the measurements. The antibody concentration in the said solution was 174 $\mu$M when the absorbance was measured at 280 nm and then the concentration was calculated by assuming that the absorptivity of the antibody solution at the concentration of 1% was 13.0 and the molecular weight was 144 kd (Seikagaku-Data-Book II, pp. 1008, edited by Nihon-Seikagakkai, published by Tokyo-Kagaku-Dohjin in 1980). By diluting this solution using the same buffer solution as that used for the dialysis, seven types of the anti-FgDP-E antibody solutions with the concentrations of 20, 30, 50, 70, 80, 100 and 120 $\mu$M, respectively, were obtained.

The PT measurements were conducted for the liquid samples of the commercially available control plasma products "Dade Ci-Trol Coagulation Control Level I" and "Dade Ci-Trol Coagulation Control Level II" diluted with these antibody solutions to study the coagulation inhibitory effect of the anti-FgDP-E antibody. Here, a commercially available "Thromboplastin C Plus" (manufactured by Dade Diagnostics of P.P. Inc.) was used as the PT reagent. The PT reagent was used in the concentration twice as much as that used regularly by regenerating the lyophilized product of the reagent with a half of the regular volume of distilled water. The molar ratios between fibrinogen contained in the liquid samples used for the measurements and the anti-FgDP-E antibody are as shown in Table 2.

TABLE 2

| The concentration of the anti FgDP-E antibody in the solution of the inhibitor, anti FgDP-E, prepared ($\mu$M) | 20.0 | 30.0 | 50.0 | 70.0 | 80.0 | 100.0 | 120.0 |
|---|---|---|---|---|---|---|---|
| The molar ratio of the anti FgDP-E/Fib when Dade Ci-trol Coagulation Control Level I is used. | 2.5 | 3.8 | 6.3 | 8.8 | 10.0 | 12.5 | 15.0 |
| The molar ratio of the anti FgDP-E/Fib when Dade Ci-trol Coagulation Control Level II is used. | 2.2 | 3.3 | 5.6 | 7.8 | 8.9 | 11.1 | 13.3 |

The PT measurements were conducted using a commercially available KC-10A (manufactured by Amelung GmbH, Lemgo) according to the following procedure.

In eight KC-10A sample cups, steal balls were placed and to each of the said sample cups, 100 $\mu$l of Dade Ci-Trol Coagulation Control Level I plasma product was added with a micropipette. After then, to seven out of the eight sample cups, 100 $\mu$l of the anti-FgDP-E antibody solution with different concentrations as shown in Table 2 were added and mixed, respectively. And to the remaining one sample cup, 100 $\mu$l of a 30 mM HEPES buffer solution (pH 7.4) containing 350 mM sodium chloride was added as a control. The eight sample cups were transferred to the measuring section and heated at 37° C. for three minutes. Finally, 100 $\mu$l of the above-mentioned PT reagent was added and the coagulation time, that is the time period until fibrin clot occured, was measured.

The each difference between the coagulation time obtained from the case in which the each anti-FgDP-E antibody solution was added and the coagulation time obtained from the control (which is abbreviated as the degree of coagulation time extension hereinafter) was calculated. And then, by plotting the molar ratio of the anti-FgDP-E antibody/Fib on the X axis and the degree of coagulation time extension on the Y axis, the effect of the anti-FgDP-E antibody addition was shown. The same procedures for the measurement were conducted for the cases using Dade Ci-Trol Coagulation Control Level II.

Figure 5:
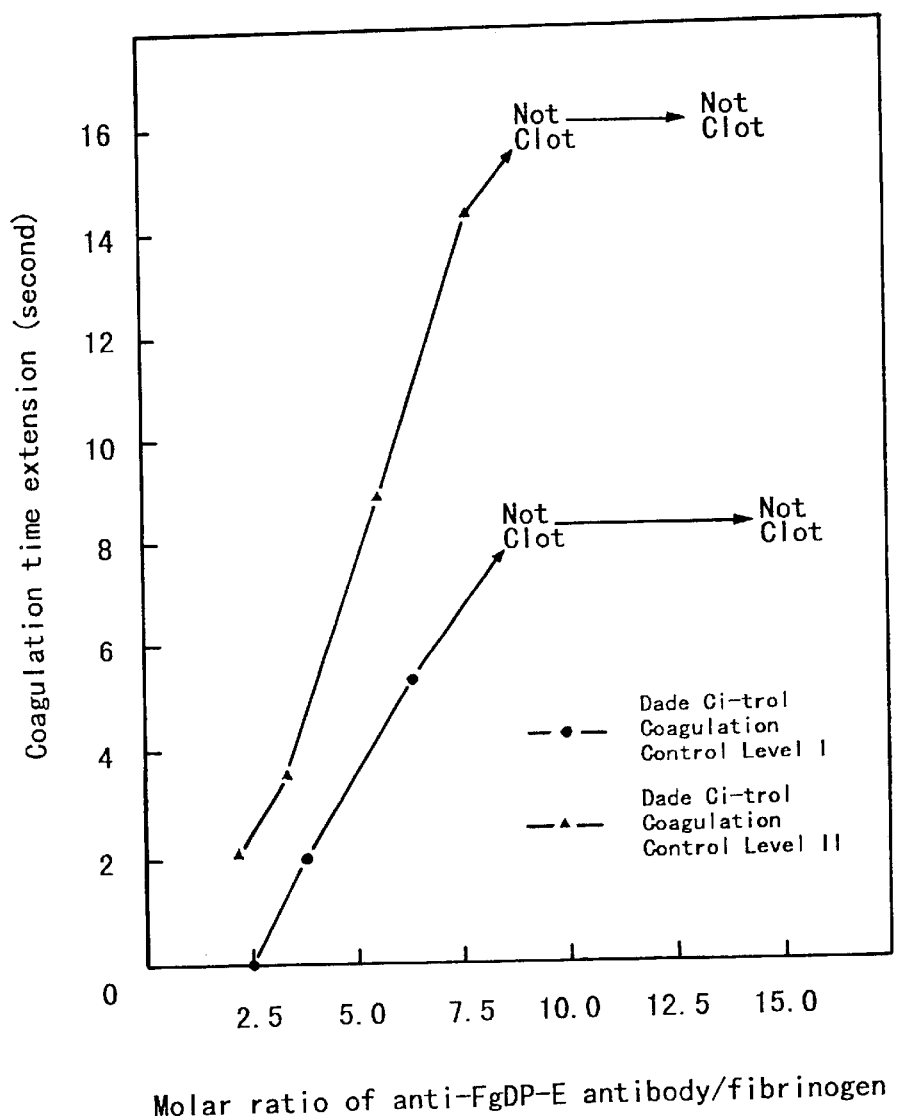
FIG. 5 shows coagulation inhibitory effects of an anti-FgDP-E antibody.

The result is shown in FIG. 5. In FIG. 5, the cases where no coagulation occurred were represented with "NOT CLOT". Fibrin coagulation was shown to begin to be avoided from the anti-FgDP-E antibody/Fib molar ratio of 8.8 with Dade Ci-Trol Coagulation Control Level I and 8.9 with Dade Ci-Trol Coagulation Control Level II. From this result, coagulation inhibitory effect of anti-FgDP-E antibody was clearly shown. And, the reaction completion product contained in the sample cup in the case that coagulation was avoided easily flowed out from the vessel by only turning the cup upside down.

EXAMPLE 1

Turbidity change which occurred in a liquid sample after contacting the liquid sample and a blood coagulation reagent at the presence of the anti-FgDP-E antibody was measured in the PT and APTT measuments to assure that the coagulation parameters can be determined from the degree of turbidity change.

(1) At the first, a qualitative correlation (a specificity) was assured between the above-mentioned degree of turbidity change and the coagulation parameters.

Here, the blood coagulation reagent, the liquid sample, the anti-FgDP-E antibody solution, the condition to measure turbidity, the PT measurement procedure and the APTT measurement procedure used are as follows.

(Blood Coagulation Reagent)
For PT measument:
  Thromboplastin C Plus (manufactured by Dade Diagnostics of P.P. Inc.) was regenerated with a half of the regular volume of distilled water
For APTT measurement:
  Dade Actin Activated Cephaloplastin Reagent·ATCC (manufactured by Dade Diagnostics of P.P. Inc.)
(A Liquid Sample)
Dade Ci-Trol Coagulation Control Level I (manufactured by Dade Diagnostics of P.P. Inc.):
  a control plasma product made of normal plasma (8 $\mu$M of the fibrinogen concentration)
Dade Ci-Trol Coagulation Control Level II (manufactured by Dade Diagnostics of P.P. Inc.):
  a control plasma product made of moderately abnormal plasma (9 $\mu$M of the fibrinogen concentration)
Dade Ci-Trol Coagulation Control Level III (manufactured by Dade Diagnostics of P.P. Inc.):
  a control plasma product made of highly abnormal plasma (8 $\mu$M of the fibrinogen concentration)
The fibrinogen concentrations were the observed values measured by using the measuring device KC-10A manufactured by Amelung GmbH, Lemgo and Dade Fibrinogen Determination Reagent (manufactured by Dade Diagnostics of P.P. Inc.).

(Anti Fg-DP-E Antibody Solution)

For the PT measurement:

a 80 μM anti-FgDP-E antibody solution which was prepared by placing the concentrated antibody solution used in the confirmation of the above-mentioned coagulation inhibitory effect of the anti-FgDP-E antibody in a dialysis membrane and dialyzed against a 30 mM HEPES (manufactured by Dojindo Laboratories; pH 7.4) solution containing 350 mM NaCl.

For the APTT measurement:

a 80 μM anti-FgDP-E antibody solution which was prepared by placing the concentrated antibody solution used in the confirmation of the above-mentioned coagulation inhibitory effect of the anti-FgDP-E antibody in a dialysis membrane and dialyzed against a 30 mM HEPES (manufactured by Dojindo Laboratories; pH 7.4) solution containing 20 mM $CaCl_2$ and 350 mM NaCl.

(Condition for Turbidity Measurement)

Measuring device: Quick Turbo 2 (manufactured by A & T Corp.)

Wavelength to be measured: 405 nm

Measuring interval: once every second (PT Measurement Procedure)

One hundred μl of the individual liquid sample was taken into a measurement cell, and to the said measurement cell 100 μl of the anti-FgDP-E antibody solution was added and then heated at 37° C. for 5 minutes. After then, 100 μl of the PT reagent was added and from this time point, the measurements of turbidity change was started with Quick Turbo 2. Here, the molar ratio of the anti-FgDP-E antibody/Fib in the reaction system was about 10.

(APTT Measurement Procedure)

One hundred μl of the individual liquid sample was taken into a measurement cell and to the said measurement cell 100 μl of the APTT measurement reagent was added and the heated at 37° C. for 5 minutes. After then, 100 μl of the Anti-FgDP-E antibody solution was added and from this time point, the measurements of turbidity change was started with Quick Turbo 2. Here, the molar ratio of the anti-FgDP-E antibody/Fib in the reaction system was about 10.

Figure 6:
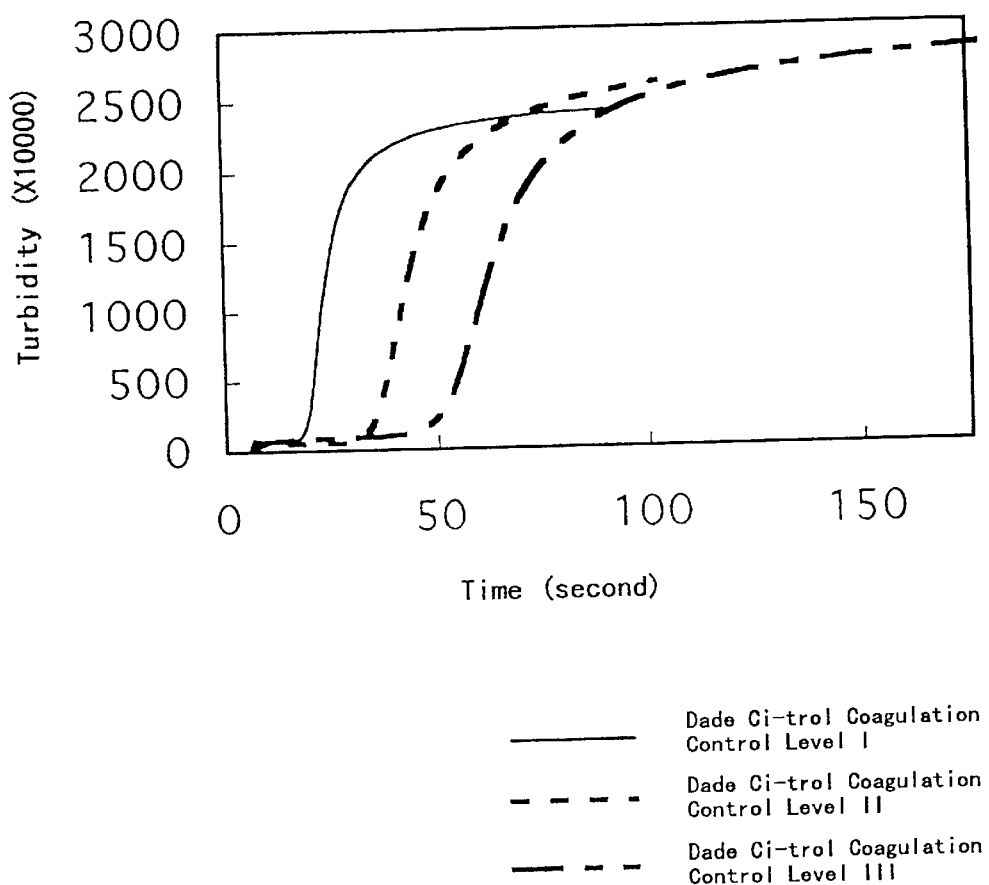
FIG. 6 shows turbidity rise curves obtained from the PT measurements using the anti-FgDP-E antibody as the coagulation inhibitor in the method of the invention.
Figure 7:
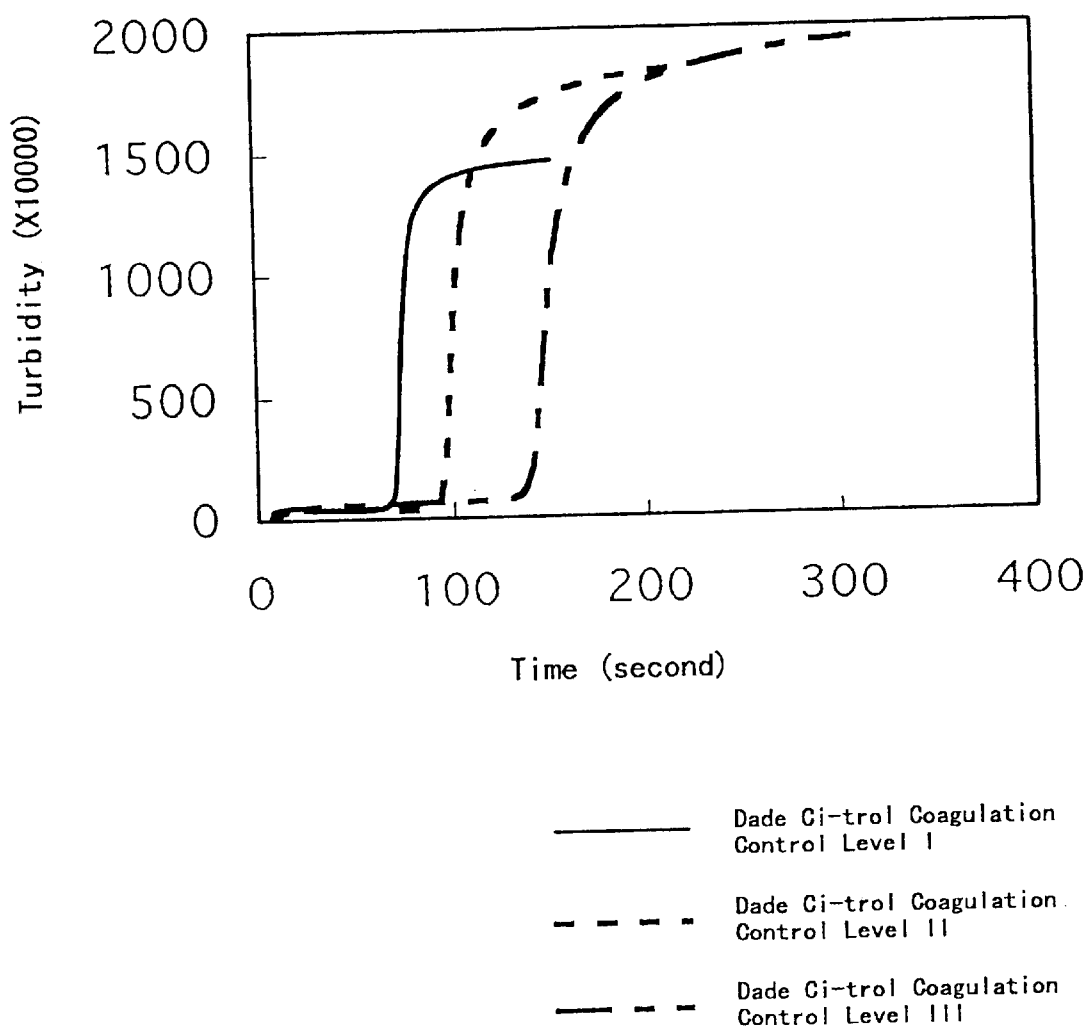
FIG. 7 shows turbidity rise curves obtained from the APTT measurements using the anti-FgDP-E antibody as the coagulation inhibitor in the method of the invention.

The results of the PT measurement and the APTT measurement are shown in FIG. 6 and FIG. 7, respectively. As shown in these figures, it was found that either the PT measurement or the APTT measurement in the system which no coagulation occurred showed an increase in its turbidity. In addition, the transition level of the turbidity increase was coincide with the degree of the coagulation abnormality of the individual liquid sample.

And, the reaction completion product contained in the measurement cell was easily removed by only turning the cell upside down.

(2) Then, reproducibility was confirmed. That is, in the similar way to that described above (1), 10 cycles of the measurements for the individual samples were conducted except that the buffer solutions used for dialysis to prepare the anti-FgDP-E antibody solutions were modified for the PT measurement and the APTT measurement as follows.

The buffer solution for the PT measurement:

a 30 mM HEPES buffer solution containing 150 mM NaCl (manufactured by Dojindo Laboratories; pH 7.4).

The buffer solution for the APTT measurement:

a 30 mM HEPES buffer solution containing 20 mM $CaCl_2$ and 150 mM NaCl (manufactured by Dojindo Laboratories; pH 7.4) was used.

Then, from the graphs of the turbidity change obtained from the individual measurements, the time period from the starting of turbidity measurement to the point where the turbidity was increased to 0.02 (as optical density) was read and defined as the putative coagulation time, and then the reproducibility of the putative coagulation times obtained from the individual measurements were evaluated in terms of CV value. The results were shown in Table 3 and Table 4 for the PT measurement and the APTT measurement, respectively. Both of the measurements show good results.

TABLE 3

| Run for the measurement | Dade Ci-trol Coagulation Control Level I (sec.) | Dade Ci-trol Coagulation Control Level II (sec.) | Dade Ci-trol Coagulation Control Level III (sec.) |
| --- | --- | --- | --- |
| 1 | 11.1 | 20.1 | 31.0 |
| 2 | 11.0 | 19.8 | 32.0 |
| 3 | 11.3 | 20.4 | 31.6 |
| 4 | 11.7 | 19.5 | 31.7 |
| 5 | 12.0 | 20.8 | 31.9 |
| 6 | 11.5 | 19.9 | 31.4 |
| 7 | 11.6 | 19.9 | 31.8 |
| 8 | 11.2 | 20.0 | 31.5 |
| 9 | 11.8 | 19.7 | 31.0 |
| 10 | 11.4 | 19.8 | 32.0 |
| Average | 11.5 | 20.0 | 31.6 |
| Standard deviation | 0.30 | 0.35 | 0.35 |
| CV (%) | 2.65 | 1.77 | 1.11 |

TABLE 4

| Run for the measurement | Dade Ci-trol Coagulation Control Level I (sec.) | Dade Ci-trol Coagulation Control Level II (sec.) | Dade Ci-trol Coagulation Control Level III (sec.) |
| --- | --- | --- | --- |
| 1 | 19.8 | 32.3 | 43.1 |
| 2 | 19.1 | 32.1 | 42.9 |
| 3 | 19.9 | 32.4 | 42.0 |
| 4 | 20.2 | 32.8 | 44.4 |
| 5 | 19.5 | 33.0 | 43.5 |
| 6 | 19.7 | 31.6 | 43.6 |
| 7 | 20.1 | 32.3 | 42.9 |
| 8 | 20.0 | 31.5 | 43.0 |
| 9 | 19.5 | 32.5 | 43.8 |
| 10 | 19.8 | 31.9 | 42.0 |
| Average | 19.8 | 32.2 | 43.1 |
| Standard deviation | 0.31 | 0.46 | 0.71 |
| CV (%) | 1.57 | 1.42 | 1.66 |

(3) Moreover, by using forty human plasma samples as the liquid samples and by comparing the putative coagulation times obtained through the measurement according to the above-mentioned procedures with the coagulation time obtained from the conventional method for PT measurement, it was verified that there is a correlation between both of the measurement results and confirmed that the coagulation parameters can be determined by the method of the invention. Here, the PT measurement according to the conventional method was conducted using Thromboplastin C Plus (manufactured by Dade Diagnostics of P.P. Inc.) as the PT reagent and KC-10A (manufactured by Amelung GmbH, Lemgo) as the measurement device, according to the individual instruction manuals thereof.

The correlation between the coagulation time obtained from the conventional method and the putative coagulation time obtained according to the method of the invention is shown as a diagram in FIG. 8. The primary regression line was shown to be Y=1.00 X−0.4391 and the coefficient of correlation 0.9902. Accordingly, the method for the measurement of the invention was confirmed to show a very good correlation for the measurement by the conventional method in which coagulation is allowed to occur.

EXAMPLE 2

The PT measurement was conducted using the same blood coagulation reagent, liquid sample and FgDP-E antibody solution as those used in Example 1 (1), and an automated analyzer Multiple Chemistry Unit 502X (manufactured by A & T Corp.) as the measurement device. The measuring parameter at the time of the measurement was as follows.

| | |
|---|---|
| The volume of sample | 40 μl |
| The anti-FgDP-E antibody solution (R1) | 60 μl |
| The PT reagent (R2) | 60 μl |
| The wave lengths to be measured | 340 nm and 795 nm |
| The time points for the measurement | 16–36 (at the interval of 18 seconds) |

According to the instruction manual of Multiple Chemistry Unit 502X, the turbidity change was measured at the interval of 18 seconds after inputting the above-mentioned individual parameters. The detailed operating procedure is illustrated hereinafter.

The individual control plasma products were taken into the sample cups, and then the anti-FgDP-E antibody solution and the PT reagent were set in the device as R1 (the first reagent) and R2 (the second reagent), respectively. After then, the measuring operations shown hereinafter were automatically conducted by the automated analyzing device Multiple Chemistry Unit 502X. In short, 40 μl of the liquid sample as the testing sample was taken into the measurement cell, and then after approximately 30 seconds, 60 μl of the anti-FgDP-E antibody solution as R1 was added to the said measurement cell and mixed. Then, after heating the said mixture for approximately 230 seconds, the PT reagent as R2 was added and the resulting turbidity change was measured.

Twenty-one cycles of the measurements were conducted in total according to the manner in which wave lengths of 340 nm and 795 nm were simultaneously measured at the interval of 18 seconds. After the measurements, the solution after the completion of the reaction was removed from the measurement cell by suction, and the cell was washed. Here, no clot formation was recognized during the measurements, no troubles such as occlusion of a nozzle occurred, the measurement cell was sufficiently washed, and the automated measurements were repeatedly conducted without any trouble.

The method for obtaining the turbidity rise curve from the discontinuous turbidity data obtained from the automated analyzer was conducted according to the manner in which the data obtained from the two wave lengths were composed and the composite data was approximated using the function described hereinafter and then finely adjusted in the Levenberg-Marquardt method.

Figure 9:
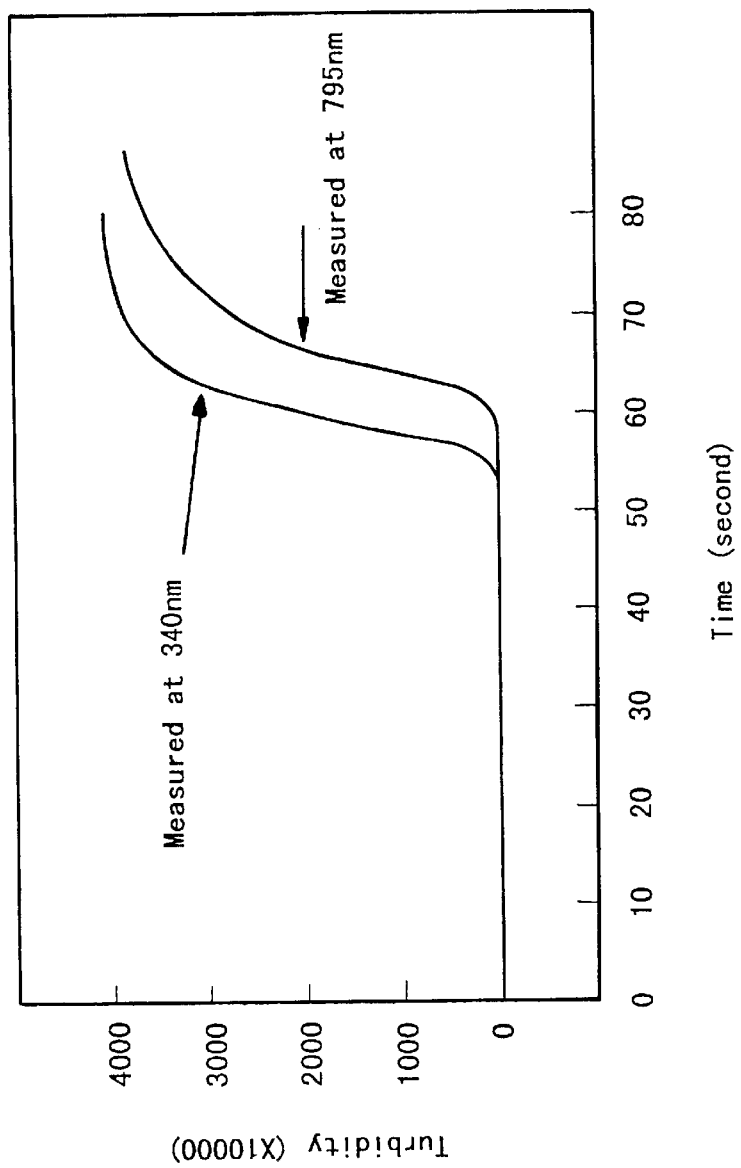
FIG. 9 is a diagram to illustrate the method to make turbidity rise curves from turbidity data obtained from the simultaneous measurements of two wave lengths.

The data were composed through taking advantage of the characteristics that the turbidity measured with the longer wavelengths (795 nm) responds relatively slower than the turbidity measured with the shorter wavelengths (340 nm) as shown in FIG. 9, according to the manner in which the turbidity data with the wavelength of 795 nm was introduced as the turbidity data with the wavelength of 340 nm taken 6 seconds before the turbidity data with the wavelength of 340 nm measured simultaneously. According to the said composite method, it was possible to increase the number of the data from 21 to 42 which were to be used in making the turbidity rise curve. In addition, the function used to approximate the composed data was the one shown in the following equation.

$$\text{Turbidity} = A \times \left[1 - \frac{1}{B \times \exp\{C \times (time - D)\} + 1}\right] - E$$

In the above-mentioned equation, A, B, C, D and E are constants, the details are as follows, and the constant A, D and E were directly calculated from the turbidity data.

A=(the maximum turbidity among the composed turbidity data)−(the minimum turbidity)

Figure 10:
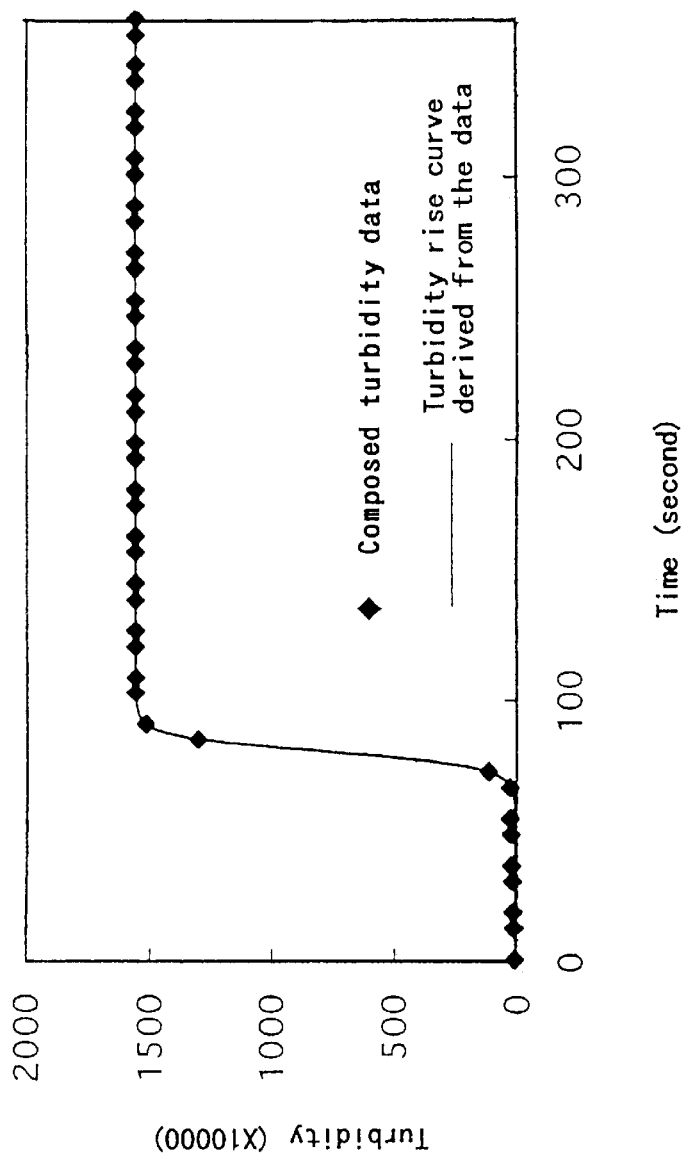
FIG. 10 is a turbidity rise curve made from a turbidity data composed.

B=a coefficient for the fine adjustment according to the Levenberg-Marquardt method C=a coefficient for the fine adjustment according to the Levenberg-Marquardt method D=the time when the degree of the turbidity change between the adjoining data among the composed turbidity data come to the maximum E=the minimum turbidity among the composed turbidity data For the function set as described above, the fine adjustments of coefficients B and C were conducted according to the Levenberg-Marquardt method. The turbidity rise curve made using the functions in which the coefficients B and C obtained by the fine adjustment according to the Levenberg-Marquardt method were substituted is shown in FIG. 10. FIG. 10 is an example of the turbidity rise curve for the case in which Dade Ci-Trol Coagulation Control Level I was measured as the liquid sample.

For the turbidity rise curve thus obtained, the time period during which the turbidity was increased by 0.02 (as optical density) from the turbidity value at the starting point was defined as the putative coagulation time.

Ten measurements were made for the individual liquid samples and the putative coagulation times were obtained according to the same procedure as that described above.

By converting the putative coagulation times obtained in the manner described above according to the equation described hereinafter, the coagulation times were obtained. Here, the equation described hereinafter was derived from the calibration curve obtained by conducting the both measurements, the conventional method and the above-mentioned method, for a series of the same liquid samples with different coagulation times.

(Coagulation time)=0.1103×(the putative coagulation time)+3.6172

The standard deviations and the CV values for evaluating the individual converted values and reproducibility are shown in Table 5. From this result, it was confirmed that a very good reproducibility can be obtained even using the automated analyzer.

TABLE 5

| Run for the measurement | Dade Ci-trol Coagulation Control Level I | Dade Ci-trol Coagulation Control Level II | Dade Ci-trol Coagulation Control Level III |
|---|---|---|---|
| 1 | 12.0 | 19.1 | 31.2 |
| 2 | 12.5 | 19.8 | 31.1 |
| 3 | 12.4 | 19.5 | 31.2 |
| 4 | 12.3 | 19.5 | 31.2 |
| 5 | 12.4 | 19.7 | 31.3 |
| 6 | 12.4 | 19.5 | 31.2 |
| 7 | 12.4 | 19.5 | 31.2 |
| 8 | 12.4 | 19.3 | 31.3 |
| 9 | 12.4 | 19.5 | 31.4 |
| 10 | 12.4 | 19.5 | 31.2 |
| Average | 12.4 | 19.5 | 31.2 |
| Standard deviation | 0.13 | 0.18 | 0.08 |
| CV value (%) | 1.04 | 0.93 | 0.26 |

EXAMPLE 3

The PT measurement and the APTT measurement were conducted in the same way as that of Example 1 (1) and (2) except that the DD solution described hereinafter was substituted for the FgDP-E antibody solution used in Example 1 (1) and (2).
(DD Solution)
For the PT measurement:

A 80 μM DD concentrate which was made by concentrating the DD purified fraction finally obtained according to the above-mentioned preparation procedure by ultrafiltration, then placing the concentrate into a dialysis membrane (manufactured by Wako Pure Chemical Industries Ltd.) and dialyzing it against a 30 mM HEPES buffer (Dojindo Laboratories; pH 7.4).

For the APTT measurement:

A 80 μM DD concentrate which was made by concentrating the purified DD fraction finally obtained according to the above-mentioned preparation procedure by ultrafiltration, then placing the concentrate in a dialysis membrane and dialyzing it against a 30 mM HEPES (Dojindo Laboratories; pH 7.4) buffer containing 20 mM $CaCl_2$.

Figure 11:
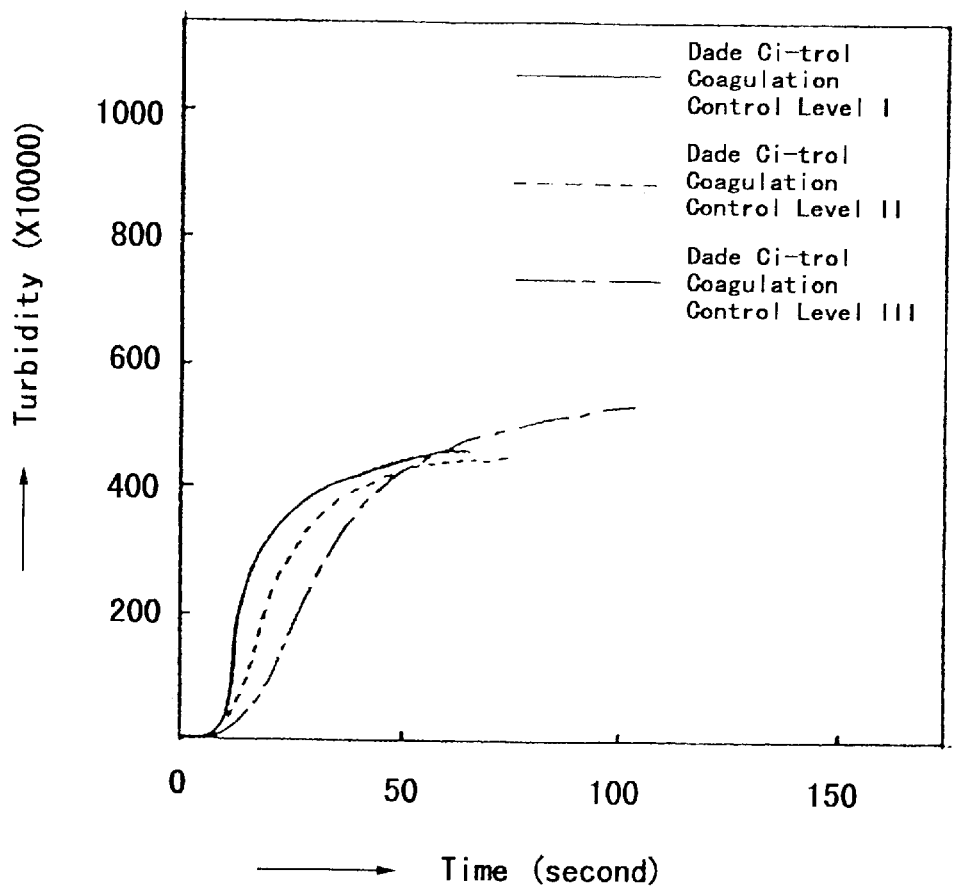
FIG. 11 shows turbidity rise curves obtained from the PT measurements in the method of the invention using fibrin degradation product D dimers as the coagulation inhibitor.
Figure 12:
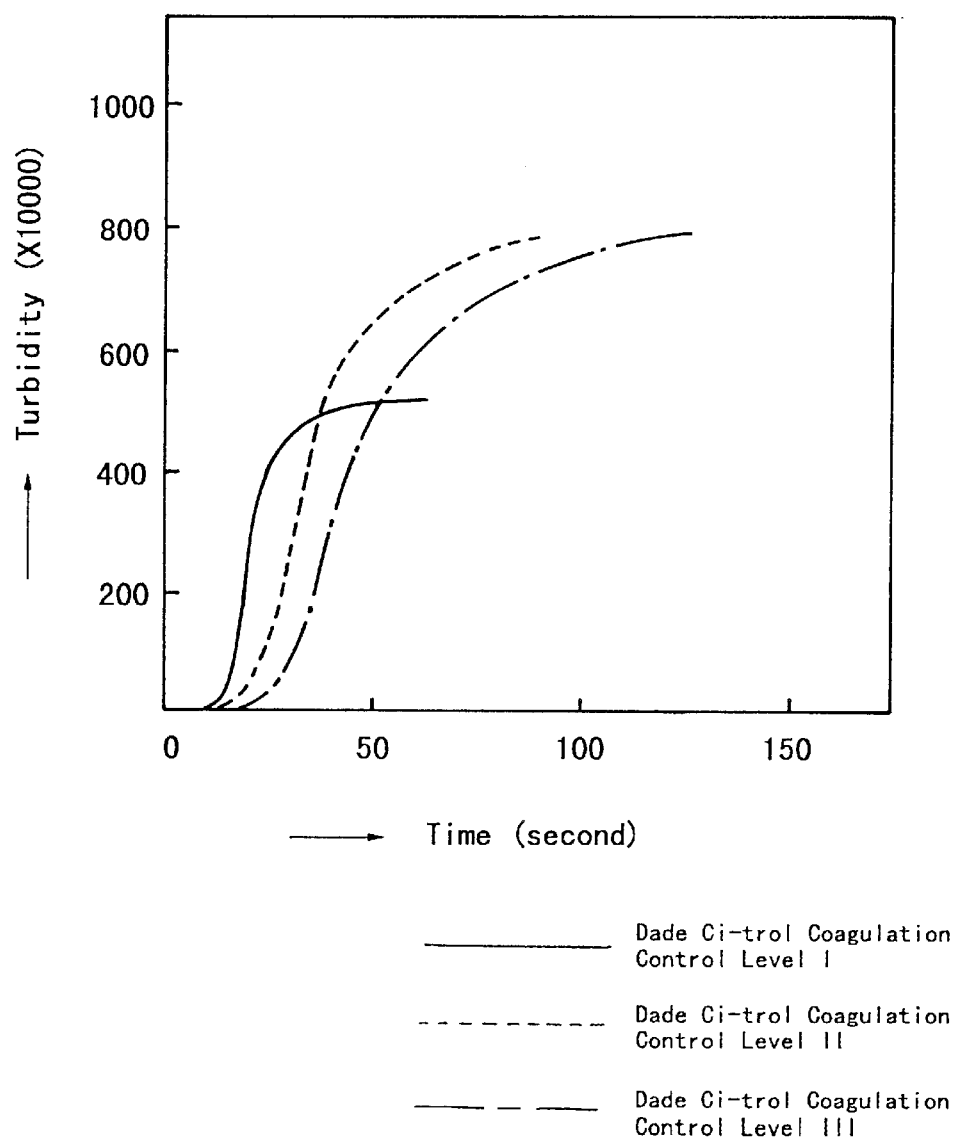
FIG. 12 shows turbidity rise curves obtained from the APTT measurements in the method of the invention using fibrin degradation product D dimers as the coagulation inhibitor.

The results of the PT measurement and the APTT measurement corresponding to Example 1 (1) are shown in FIG. 11 and FIG. 12, respectively. And the results of the PT measurement and the ATTP measurement corresponding to Example 1 (2) are shown in Table 6 and Table 7, respectively. Specificity of turbidity change in the case where DD was used as the coagulation inhibitor as well as good reproducibility were confirmed, leading to the confirmation that the coagulation parameters can be determined by measuring turbidity change, like as the case where the anti-FgDP-E antibody was used.

TABLE 6

| Run for the measurement | Dade Ci-trol Coagulation Control Level I | Dade Ci-trol Coagulation Control Level II | Dade Ci-trol Coagulation Control Level III |
|---|---|---|---|
| 1 | 13.0 | 19.6 | 26.0 |
| 2 | 12.5 | 20.5 | 26.5 |
| 3 | 12.6 | 20.6 | 26.4 |
| 4 | 13.0 | 20.5 | 25.9 |
| 5 | 12.9 | 19.7 | 26.8 |
| 6 | 12.5 | 19.8 | 27.0 |
| 7 | 12.6 | 19.8 | 27.5 |
| 8 | 12.8 | 20.4 | 27.4 |
| 9 | 13.4 | 20.3 | 25.9 |
| 10 | 13.0 | 20.0 | 26.4 |
| Average | 12.8 | 20.1 | 26.6 |
| Standard deviation | 0.27 | 0.36 | 0.55 |
| CV value (%) | 2.12 | 1.79 | 2.08 |

TABLE 7

| Run for the measurement | Dade Ci-trol Coagulation Control Level I | Dade Ci-trol Coagulation Control Level II | Dade Ci-trol Coagulation Control Level III |
|---|---|---|---|
| 1 | 19.0 | 27.5 | 35.0 |
| 2 | 20.0 | 28.0 | 36.0 |
| 3 | 19.5 | 28.5 | 35.5 |
| 4 | 19.6 | 28.0 | 35.9 |
| 5 | 19.7 | 28.4 | 35.8 |
| 6 | 19.8 | 28.3 | 36.0 |
| 7 | 19.7 | 28.2 | 37.1 |
| 8 | 19.8 | 28.0 | 35.5 |
| 9 | 19.3 | 28.1 | 36.2 |
| 10 | 20.1 | 27.8 | 36.8 |
| Average (sec.) | 19.7 | 28.1 | 36.0 |
| Standard deviation | 0.31 | 0.28 | 0.59 |
| CV value (%) | 1.56 | 0.99 | 1.63 |

EXAMPLE 3

By using the liquid samples, R1 reagent and R2 reagent described hereinafter and conducting the PT measurement using a photodiode array spectrophotometer (manufactured by Shimazu Corporation), the correlation between the degree of absorbance change of the liquid samples after contacting with the reagents and the coagulation times obtained by the conventional method was investigated.
(The Liquid Samples)
Five types of samples, A through E, were used.

Here, the coagulation times obtained for the sample A through E using the conventional method were 13.2 seconds, 17.7 seconds, 19.4 seconds, 20.5 seconds and 23.3 seconds, respectively. The coagulation times obtained according to such a conventional method are those measured using Ortho recombiplastin *1.0 (manufactured by Ortho Diagnostic Corp.) as the reagent and KC-10A (manufactured by Amelung GmbH, Lemgo) as the measuring device.
(R1 Reagent)

At the first, Ortho recombiplastin *1.0 PRT reagent (manufactured by Ortho-clinical Diagnostics KK, a lyophilized product) was regenerated with a regular amount of distilled water to produce a tissue thromboplastin solution. Then, the anti-human FDP-D antibody (manufactured by Medical Biological Laboratories, in Japan) was dialyzed against a 50 mM Tris-HCl solution (pH 7.6) containing 0.25M NaCl to generate the antibody solution. Finally, 175 μl of distilled water, 300 μl of the tissue thromboplastin solution, and 100 μl of the antibody solution were mixed at this ratio to make the R1 reagent solution.

(R2 Reagent Solution)

At the first, TESTZYM chromogenic substrate S-2238 (manufactured by Daiichi Pure Chemical Corporation) was regenerated with a regular amount of distilled water to obtain the chromogenic substrate solution. Finally, 150 μl of the chromogenic substrate solution and 150 μl of Ortho recombiplastin *1.0 PRT reagent solution (manufactured by Ortho-clinical Diagnostics KK, calcium chloride solution) were mixed at this ratio to make the R2 reagent solution.

Contact of the liquid sample and the reagent and the following measurement of absorbance changes were conducted as follows. In detail, 575 μl of the R1 was taken into the measurement cell, then 25 μl of the liquid sample as the test sample was added to the measurement cell and mixed, then after the said mixture was heated at 37° C. for 180 seconds, 300 μl of the R2 was added and mixed. Then the change in absorbance at 405 nm in the reaction system was measured using the photodiode array spectrophotometer (manufactured by Shimazu Corporation). Here, the reaction completion product contained in all the measurement cells easily flowed out from the vessel by only turning the cells upside down. The result of the measurement for Sample A is shown in FIG. 13.

In the reaction system, when p-nitroaniline (pNA) is freed through the reaction between the resulting thrombin and TESTZYM chromogenic substrate S-2238, the absorbance at 405 nm will change. As it is believed that the shorter the coagulation time is, the more thrombin is resulted in the reaction system, when there exists a reverse correlation between the both, it is possible to obtain the coagulation time by detecting the degree of the absorbance change.

The relationship between the degree of absorbance change during the period of from the addition of the R2 reagent through the time of 600 seconds later (ΔOD) and the coagulation time measured by the conventional method is shown in Table 8. As shown in the table, as the clear reverse correlation exists between the coagulation time obtained by the conventional method and the above-mentioned degree of absorbance change, it was confirmed that the coagulation time can be obtained by detecting changes in absorbance.

TABLE 8

| Measured sample | The conventional method | ΔOD |
| --- | --- | --- |
| Sample A | 13.2 sec. | 0.620 |
| Sample B | 17.7 sec. | 0.480 |
| Sample C | 19.4 sec. | 0.200 |
| Sample D | 20.5 sec. | 0.120 |
| Sample E | 23.3 sec. | 0.080 |

LIST OF REFERENCES

1. Kudryx, B. J. et al., (1974) J. Biol. Chem. 249, 3322–3325

Abstract; Bindings among fibrin monomers are raised by the interaction of the complementary sites which is called the polymerization site. The polymerization site "a" existing within the D region is indigenous to fibrinogen molecule.

2. Laudano, A. P. et al., (1978) Proc. Natl. Acad. Sci. U.S.A. 75, 3085–3089, and Laudano, A. P. et al., (1981) Science 212, 457–459

Abstract; Fibrinogen exposes the polymerization site "A" on the E region through digestion and release of fibrinopeptide A by thrombin. As the E region is in the dimeric structure, it is assumed that two copies of the polymerization site "A" exist within the E region.

3. Fowler, W. E. et al., (1981) Proc. Natl. Acad. Sci. U.S.A 78, 4872–4876, and Hantgan, R. R. et al., (1979) J. Biol. Chem. 254, 11272–11281

Abstract; Through non-covalent bond between the polymerization site "a" and the polymerization site "A", double-stranded protofibrils are formed in which fibrin monomers bind each other in a half-staggered orientation, and through two-dimensional bindings and then three-dimensional bindings of the said protofibrils finally, aggregation of protofibrils results in the formation of a fibrin clot.

4. Chen R. et al., (1971) Biochemistry 10, 4486–4491

Abstract; Thrombin utilized not only fibrinogen but also blood coagulation factor XIII (XIII) as its substrate. Blood coagulation factor XIII (XIII) is turned to be activated factor XIII (XIIIa) through actions of thrombin. XIIIa allows isopeptide bonds (—CO·NH—) to be formed between the lysine residue existing within the D region of fibrin monomer molecule (located at around the C terminal of the γ chain) and the glutamine residue existing within the D region of the other fibrin monomer (located at around the C terminal of the γ chain) at the presence of $Ca^{2+}$. This effect generates cross-linking between fibrin monomers, resulting in stable fibrin.

5. Pandya, B. V. et al., (1991) Biochemistry 30, 162–168

Abstract; Thrombin makes a digest between the fourteenth Arg from the N terminal of the fibrinogen β chain and the fifteenth Gly from the N terminal of fibrinogen β chain to allow fibrinopeptide B to be released and the polymerization site B to be exposed.

What is claimed is:

1. A method for determining at least one coagulation parameter of a fluid sample comprising fibrinogen, said coagulation parameter being in a coagulation system comprising a coagulation process accompanied by limited degradation of fibrinogen with thrombin, said method comprising:

A. contacting said fluid sample comprising fibrinogen with a blood coagulation reagent in the presence of a material which inhibits the formation of fibrin polymers from fibrin monomers in said coagulation process, said material being in an amount effective to avoid the formation of fibrin clot and fibrin net, B. detecting a degree of change in a physical value of said sample triggered by said contact, said physical value being selected from the group consisting of turbidity, viscosity, permittivity, and absorbance with a coexisting chromogenic substrate, and C. evaluating said degree of change in said physical value as an indicator to show the coagulation parameter, said coagulation parameter being at least one parameter(s) selected from the group consisting of (i) prothrombin time, (ii) activated partial thromboplastin time, (iii) fibrinogen concentration, (iv) thrombotest % activity, (v) hepaplastin test % activity, (vi) Protein C % activity, (vii) Protein S % activity, (viii) content of blood coagulation factor II, factor V, factor VII, or factor X, and (ix) content of blood coagulation factor VIII, factor IX, factor XI or factor XII.

2. The method according to claim 1, further comprising comparing said degree of change in said physical value of step C with the degree of change in same physical value of a standard sample.

3. The method according to claim 1, wherein said degree of change in said physical value of step B is measured before precipitation of a fibrin clot in said fluid sample.

4. The method according to claim 1, wherein said fluid sample is whole blood or plasma derived from a warm blooded animal, a prepared solution thereof, or a fibrinogen-containing solution.

5. The method according to claim 1, wherein said material which inhibits the formation of fibrin polymers from fibrin monomers is selected from the group consisting of peptides or proteins which bind to the E region of fibrin monomer, and peptides or proteins which bind to the D region of fibrin monomer.

6. The method according to claim 5, wherein the peptides or proteins which bind to the E region of fibrin monomer is selected from the group consisting of polyclonal antibodies against fibrinogen degradation product E, polyclonal antibodies against fibrin degradation product E, and fibrin degradation products comprising the D segment.

7. The method according to claim 6, wherein the fibrin degradation products comprising the D segment is D dimer itself.

8. The method according to claim 5, wherein the peptides or proteins which bind the D region of fibrin monomer is selected from the group consisting of antibodies against fibrin degradation product D dimer and fibrinogen degradation product D monomer.

9. The method according to claim 1, wherein said material which inhibits the formation of fibrin polymers from fibrin monomers is in a concentration of 1–50 mg/ml.

10. The method according to claim 1, wherein said blood coagulation reagent is at least one type(s) of reagent(s) selected from the group consisting of reagent comprising materials with negative charge on its surface (activator) and cephalin, reagent comprising thrombin, blood coagulation reagents which comprise one or more factors among the whole series of blood coagulation factors and lack any of those factors, Protein C activating reagents, and optionally reagents which comprise an inorganic salt.

11. A kit for determination of a coagulation parameter, which kit comprises a material which inhibits the formation of fibrin polymers from fibrin monomers, a blood coagulation reagent, and a standard sample whose coagulation parameter is known, said coagulation parameter being at least one parameter(s) selected from the group consisting of (i) prothrombin time, (ii) activated partial thromboplastin time, (iii) fibrinogen concentration, (iv) thrombotest % activity, (v) hepaplastin test % activity, (vi) Protein C % activity, (vii) Protein S % activity, (viii) content of blood coagulation factor II, factor V, factor VII or factor X, and (ix) content of blood coagulation factor VIII, factor IX, factor XI or factor XII, said material being in an amount effective to avoid the formation of fibrin clot and fibrin net.

12. The kit according to claim 11, wherein the material which inhibits the formation of fibrin polymers from fibrin monomers is a peptide or protein which binds to the E region of fibrin monomer.

* * * * *